(12) United States Patent
Dewdney et al.

(10) Patent No.: US 7,608,603 B2
(45) Date of Patent: Oct. 27, 2009

(54) SUBSTITUTED PYRAZOLO[3,4-D] PYRIMIDINES AS P38 MAP KINASE INHIBITORS

(75) Inventors: Nolan James Dewdney, San Jose, CA (US); Tobias Gabriel, San Francisco, CA (US); Kristen Lynn McCaleb, Daly City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 174 days.

(21) Appl. No.: 11/509,121

(22) Filed: Aug. 23, 2006

(65) Prior Publication Data
US 2007/0049597 A1 Mar. 1, 2007

Related U.S. Application Data

(60) Provisional application No. 60/712,007, filed on Aug. 25, 2005.

(51) Int. Cl.
C07F 9/09 (2006.01)
C07D 487/04 (2006.01)
A61K 31/519 (2006.01)
A61K 31/661 (2006.01)
A61P 11/16 (2006.01)
A61P 19/02 (2006.01)

(52) U.S. Cl. ............... 514/81; 514/262.1; 544/244; 544/262

(58) Field of Classification Search .......... 544/118, 544/244, 262; 514/234.5, 81, 262.1
See application file for complete search history.

(56) References Cited

U.S. PATENT DOCUMENTS

| 6,383,790 B1 | 5/2002 | Shokat |
| 2004/0180896 A1 | 9/2004 | Munson et al. |
| 2005/0197340 A1 | 9/2005 | Arora et al. |

FOREIGN PATENT DOCUMENTS

WO WO 2004/11303 A1 9/2005

*Primary Examiner*—Brenda L Coleman
*Assistant Examiner*—Susanna Moore
(74) *Attorney, Agent, or Firm*—Robert C. Hall

(57) ABSTRACT

Compounds of formula Ia, Ib, Ic, Id, Ie, If, Ig or Ih:

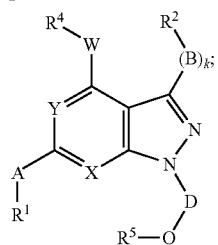

Ia

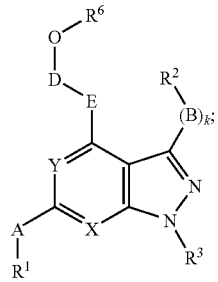

Ib

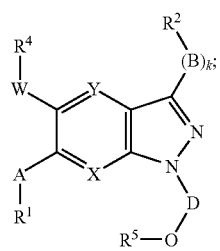

Ic

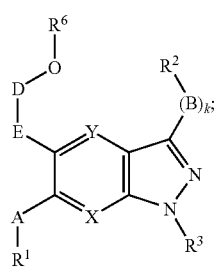

Id

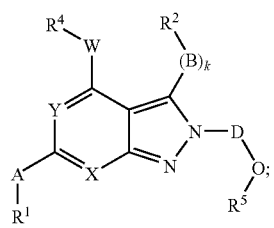

Ie

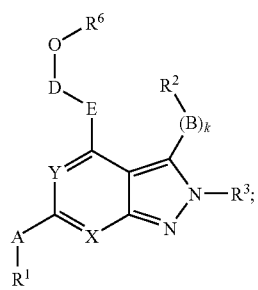

If

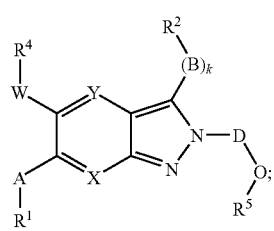

Ig

-continued
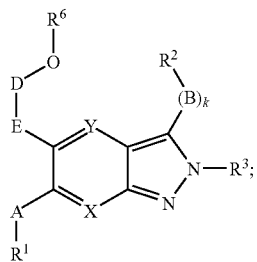
Ih
wherein X and Y are nitrogen or one of X and Y is nitrogen and the other is $CR^g$, and W, D, E, $R^4$, $R^5$, $R^6$ and $R^g$ are as defined herein. Also disclosed are methods of making the subject compounds and methods of using the compounds in the treatment of p38 MAP kinase-mediated diseases.
10 Claims, No Drawings

SUBSTITUTED PYRAZOLO[3,4-D]PYRIMIDINES AS P38 MAP KINASE INHIBITORS

CROSS-REFERENCE TO RELATED APPLICATIONS

This application is entitled to the benefit of provisional patent application Ser. No. 60/712,007 filed on Aug. 25, 2005, the disclosure of which is incorporated herein by reference.

FIELD OF THE INVENTION

The present invention relates to fused pyrazolo pyrimidine derivatives and related compounds, a process for their manufacture, pharmaceutical preparations comprising the same, and methods for using the same. More specifically, useful prodrug compounds of fused pyrazolo pyrimidines and related compounds are disclosed, together with methods for making and using of the same.

BACKGROUND OF THE INVENTION

Mitogen-activated protein kinases (MAP) is a family of proline-directed serine/threonine kinases that activate their substrates by dual phosphorylation. The kinases are activated by a variety of signals including nutritional and osmotic stress, UV light, growth factors, endotoxin and inflammatory cytokines. One group of MAP kinases is the p38 kinase group that includes various isoforms (e.g., p38α, p39β, p38γ and p38δ). The p38 kinases are responsible for phosphorylating and activating transcription factors as well as other kinases, and are activated by physical and chemical stress, pro-inflammatory cytokines and bacterial lipopolysaccharide.

More importantly, the products of the p38 phosphorylation have been shown to mediate the production of inflammatory cytokines, including TNF and IL-1, and cyclooxygenase-2. Each of these cytokines has been implicated in numerous disease states and conditions. For example, TNF-α is a cytokine produced primarily by activated monocytes and macrophages. Its excessive or unregulated production has been implicated as playing a causative role in the pathogenesis of rheumatoid arthritis. More recently, inhibition of TNF production has been shown to have broad application in the treatment of inflammation, inflammatory bowel disease, multiple sclerosis and asthma.

TNF has also been implicated in viral infections, such as HIV, influenza virus, and herpes virus including herpes simplex virus type-1 (HSV-1), herpes simplex virus type-2 (HSV-2), cytomegalovirus (CMV), varicella-zoster virus (VZV), Epstein-Barr virus, human herpes virus-6 (HHV-6), human herpesvirus-7 (HHV-7), human herpesvirus-8 (HHV-8), pseudorabies and rhinotracheitis, among others.

Similarly, IL-1 is produced by activated monocytes and macrophages, and plays a role in many pathophysiological responses including rheumatoid arthritis, fever and reduction of bone resorption.

Additionally, the involvement of p38 has been implicated in stroke, Alzheimer's disease, osteoarthritis, lung injury, septic shock, angiogenesis, dermatitis, psoriasis and atopic dermatitis. *J. Exp. Opin. Ther. Patents,* 2000, 10(1).

The role of p38 MAP kinase as a therapeutic target in oncology has been reviewed: Podar, K. H.; Teru; Chauhan, Dharminder; Anderson, Kenneth C., "Targeting signalling pathways for the treatment of multiple myeloma", *Expert Opinion on therapeutic Targets* 2005, 9, 359-381; Schultz, R. M., "Potential of p38 MAP kinase inhibitors in the treatment of cancer", *Progress in Drug Research* 2003, 60, 59-92.

The inhibition of these cytokines by inhibition of the p38 kinase is of benefit in controlling, reducing and alleviating many of these disease states.

Chemical derivatization of active drug moieties is frequently undertaken for a variety of reasons including modification of the physical properties of the active drug, optimization of the pharmacokinetic parameters and site-specific targeting or localization of the active moiety to specific target tissues or cells. Albert introduced the term prodrug to describe a compound which lacks intrinsic biological activity but which is capable of metabolic transformation to the active drug substance (A. Albert, *Selective Toxicity*, Chapman and Hall, London, 1951). While the metabolic transformation can catalyzed by specific enzymes, often hydrolases, the active compound can also be released by non-specific chemical processes. Produgs have been recently reviewed (P. Ettmayer et al., *J. Med Chem.* 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amersterdam 1985).

SUMMARY

The invention provides compounds of formula Ia, Ib, Ic, Id, Ie, If, Ig or Ih:

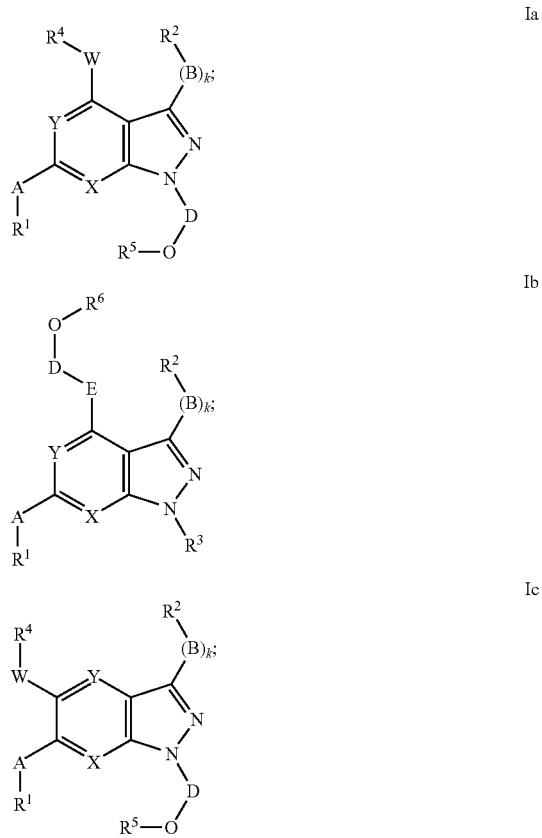

-continued

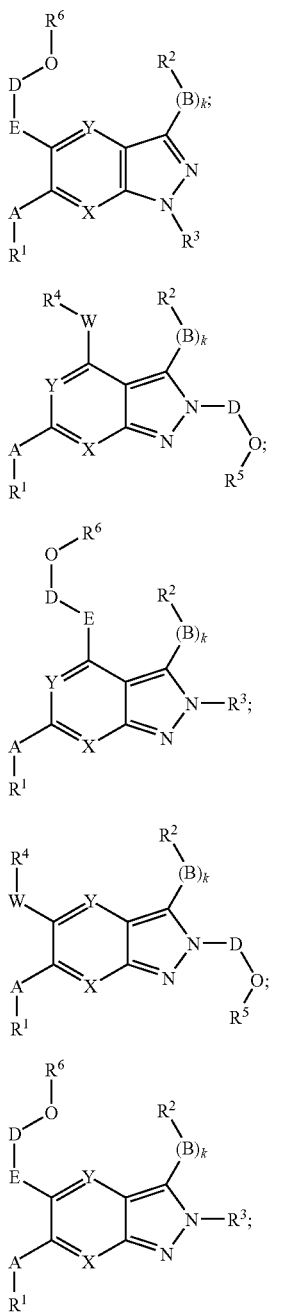

or a pharmaceutically acceptable salt thereof, wherein:
R$^1$ is aryl, heteroaryl, aralkyl or cycloalkyl;
R$^2$ is aryl, heteroaryl, cycloalkyl, branched alkyl, heterocyclyl, hydroxyalkyl, cycloalkenyl or hydroxycycloalkyl;
R$^3$ is hydrogen or alkyl;
R$^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, —(CHR$^a$)$_r$—C(=O)—R$^b$, —(CHR$^a$)$_r$—O—C(=O)—R$^b$, —(CHR$^a$)$_r$—NH—C(=O)—R$^b$ or —SO$_2$—R$^b$, wherein
R$^a$ is hydrogen, alkyl or heteroalkyl;
R$^b$ is alkyl, hydroxy, amino, heteroalkyl, aryl, aralkyl, heteroaryl, or heterocyclyl;
r is from 0 to 4;
R$^5$ is hydrogen, —C(=O)—R$^c$, —(O=)P(OR$^d$)$_2$, —S(=O)$_2$OR$^d$, or a mono-, di- or tri-peptide;
R$^6$ is —C(=O)—R$^c$ or —(O=)P(OR$^d$)$_2$—, —S(=O)$_2$OR$^d$, or a mono-, di- or tri-peptide;
wherein
R$^c$ is alkyl, alkoxy, amino, cycloalkyl, cycloalkylalkyl, aryl, arylalkyl, heteroaryl, heteroarylalkyl, cycloalkyloxy, cycloalkylalkyloxy, aryloxy, arylalkyloxy, heteroaryloxy, heteroarylalkyloxy, heterocyclyl, heterocylyloxy, —(CH$_2$)$_p$—C(=O)—R$^e$, —(CH=CH)—C(=O)—R$^e$, or —CH(NH$_2$)—R$^f$;
wherein
R$^e$ is hydrogen, hydroxy, alkoxy or amino;
p is 2 or 3;
R$^f$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl;
R$^d$ is hydrogen, alkyl, an alkalai metal ion or an alkaline earth metal ion;
X and Y are nitrogen, or one of X and Y is nitrogen and the other is CR$^g$;
wherein
R$^g$ is hydrogen, alkyl, hydroxy, alkoxy, amino, haloalkyl, cyano, halo, heteroalkyl, C(=O)—R$^h$ or —SO$_2$—R$^h$,
wherein
R$^h$ is hydrogen or alkyl;
D is —(CR$^7$R$^8$)$_n$—;
wherein
n is from 1 to 3;
R$^7$ and R$^8$ each independently is hydrogen or alkyl;
W is a bond, O, S(O)$_q$, CH$_2$ or NR$^i$;
E is O, S(O)$_q$, CH$_2$ or NR$^i$;
wherein
q is from 0 to 2;
R$^i$ is hydrogen, alkyl, heteroalkyl, heterocyclyl, hydroxycycloalkyl, —C(=O)—R$^j$ or —SO$_2$—R$^j$,
wherein
R$^j$ is alkyl, aryl, aralkyl, heteroaryl, heteroalkyl or heterocyclyl;
or R$^4$ and R$^i$ together with the atoms to which they are attached may form a heterocyclic ring;
A is O, CH$_2$, S(O)$_s$, C(=O), NR$^k$, or CH(OR$^k$),
wherein
s is from 0 to 2;
R$^k$ is hydrogen or alkyl,
k is 0 or 1;
B is O, S(O)$_j$, —(CHR$^m$)$_t$, —NR$^m$SO$_2$—, NR$^m$, NR$^m$C(=O) or C(=O),
wherein
j is 0, 1 or 2;
t is from 1 to 3; and
R$^m$ is hydrogen or alkyl.

Another aspect of the invention provides a pharmaceutical formulation comprising one or more compounds of formula I and a pharmaceutically acceptable carrier, diluent, and/or excipient therefor.

Compounds of the invention are inhibitors of protein kinases, and exhibit effective activity against p38 in vivo. They are selective for p38 kinase relative to cyclin-dependent kinases and tyrosine kinases. Therefore, compounds of the present invention can be used for the treatment of diseases mediated by the pro-inflammatory cytokines such as TNF and IL-1. Thus, another aspect of the present invention provides a method for treating p38 mediated diseases or conditions in which a therapeutically effective amount of one or more compounds of formula I is administered to a patient.

DETAILED DESCRIPTION OF THE INVENTION

All publications cited in this disclosure are incorporated herein by reference in their entirety.

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means a linear saturated monovalent hydrocarbon moiety of one to six carbon atoms or a branched saturated monovalent hydrocarbon moiety of three to six carbon atoms, e.g., methyl, ethyl, propyl, 2-propyl, n-butyl, iso-butyl, tert-butyl, pentyl, and the like.

"Alkylene" means a linear saturated divalent hydrocarbon moiety of one to six carbon atoms or a branched saturated divalent hydrocarbon moiety of three to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like. "Alkenlene" means a divalent alkenyl radical.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like. "Alkynylene" means a divalent alkynyl radical.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Alkylsulfonyl" means a moiety of the formula —$SO_2$R wherein R is alkyl as defined herein.

"Alkalai metal ion" means a monovalent ion of a group Ia metal such as lithium, sodium, potassium, rubidium or cesium, preferably sodium or potassium.

"Alkaline earth metal ion" means a divalent ion of a group IIA metal such as berylium, magnesium, calcium, strontium or barium, preferably magnesium or calcium.

"Amino" means a group —NR'R" wherein R' and R" each independently is hydrogen or alkyl. "Amino" as used herein thus encompasses "alkylamino" and "dialkylamino".

"Alkylaminoalkyl" means a group —R—NHR' wherein R is alkylene and R' is alkyl. Alkylaminoalkyl includes methylaminomethyl, methylaminoethyl, methylaminopropyl, ethylaminoethyl and the like.

"Dialkylaminoalkyl" means a group —R—NR'R" wherein R is alkylene and R' and R" are alkyl as defined herein. Dialkylaminoalkyl includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aryl" means a monovalent monocyclic or bicyclic aromatic hydrocarbon moiety which is optionally substituted with one or more, preferably one, two or three, substituents, each of which is preferably selected from the group consisting of alkyl, hydroxy, alkoxy, haloalkyl, haloalkoxy, halo, nitro, cyano, amino, mono- and dialkylamino, methylenedioxy, ethylenedioxy, acyl, heteroalkyl, optionally substituted aryl, optionally substituted heteroaryl, optionally substituted aralkyl, and optionally substituted heteroaralkyl. A particularly preferred aryl substituent is halide. More specifically the term aryl includes, but is not limited to, phenyl, 1-naphthyl, 2-naphthyl, and the like, each of which can be substituted or unsubstituted.

"Aralkyl" refers to a moiety of the formula —R—R' wherein R is alkylene and R' is aryl as defined herein.

"Aralkoxy" means a group —O—R—R' wherein R is alkylene and R' is aryl as defined herein "Substituted aralkyl" or "optionally substituted aralkyl" refers to aralkyl in which the aryl moiety is substituted or optionally substituted, respectively.

"Cycloalkyl" refers to a saturated monovalent cyclic hydrocarbon moiety of three to seven ring carbons e.g., cyclopropyl, cyclobutyl, cyclohexyl, 4-methyl-cyclohexyl, and the like. Cycloalkyl may optionally be substituted with one or more substituents, preferably one, two or three, substituents. Preferably, cycloalkyl substituent is selected from the group consisting of alkyl, hydroxy, alkoxy, haloalkyl, haloalkoxy, halo, amino, mono- and dialkylamino, heteroalkyl, acyl, aryl and heteroaryl.

"Cycloalkylalkyl" refers to a moiety of the formula $R^c$—$R^d$—, where $R^c$ is cycloalkyl and $R^d$ is alkylene as defined herein.

"Halo", "halogen" and "halide" are used interchangeably herein and refer to fluoro, chloro, bromo, or iodo. Preferred halides are fluoro and chloro with fluoro being a particularly preferred halide.

"Haloalkyl" means alkyl substituted with one or more same or different halo atoms, e.g., —$CH_2Cl$, —$CF_3$, —$CH_2CF_3$, —$CH_2CCl_3$, and the like.

"Heteroalkyl" means an alkyl moiety as defined herein wherein one or more, preferably one, two or three, hydrogen atoms have been replaced with a substituent independently selected from the group consisting of —$OR^a$, —$NR^bR^c$ (where n is 0 or 1 if $R^b$ and $R^c$ are both independently alkyl, cycloalkyl or cycloalkylalkyl, and 0 if not) and —$S(O)_nR^d$ (where n is an integer from 0 to 2), with the understanding that the point of attachment of the heteroalkyl moiety is through a carbon atom, wherein $R^a$ is hydrogen, acyl, alkoxycarbonyl, alkyl, hydroxyalkyl, alkoxyalkyl, alkylsulfonyl, aminocarbonyl, aminosulfonylamino, cycloalkyl, or cycloalkylalkyl; $R^b$ and $R^c$ are independently of each other hydrogen, acyl, alkoxycarbonyl, aminocarbonyl, aminocarbonyl, aminosulfonylamino, hydroxyalkyl, alkoxyalkyl, alkylsulfonyl, cycloalkyl, cycloalkylalkyl, alkylsulfonyl, aminosulfonyl, mono- or di-alkylaminosulfonyl, aminoalkyl, mono- or di-alkylaminoalkyl, hydroxyalkyl, alkoxyalkyl, hydroxyalkylsulfonyl or alkoxyalkylsulfonyl; and when n is 0, $R^d$ is hydrogen, alkyl, cycloalkyl, cycloalkylalkyl, or aryl, and when n is 1 or 2, $R^d$ is alkyl, cycloalkyl, cycloalkylalkyl, hydroxyalkyl, alkoxyalkyl, alkylamino, aminocarbonyl, aminosulfonylamino, alkylsulfonyl, amino, or optionally substituted phenyl. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like. Accordingly, hydroxyalkyl and alkoxyalkyl are subset of heteroalkyl.

"Heteroaryl" means a monovalent monocyclic or bicyclic moiety of 5 to 12 ring atoms having at least one aromatic ring containing one, two, or three ring heteroatoms selected from N, O, or S (preferably N or O), the remaining ring atoms being C, with the understanding that the attachment point of the heteroaryl moiety will be on an aromatic ring. The heteroaryl ring is optionally substituted independently with one or more substituents, preferably one, two or three substituents, each of which is independently selected from alkyl, haloalkyl, hydroxy, alkoxy, halo, nitro and cyano. More specifically the term heteroaryl includes, but is not limited to, pyridyl, furanyl, thienyl, thiazolyl, isothiazolyl, triazolyl, imidazolyl, isoxazolyl, pyrrolyl, pyrazolyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof.

"Heteroaralkyl" refers to a moiety of the formula —R—R' wherein R is alkylene and R' is heteroaryl as defined herein.

"Heteroaralkoxy" means a group —O—R—R' wherein R is alkylene and R' is heteroaryl as defined herein.

"Heterocyclyl" means a saturated or unsaturated non-aromatic cyclic moiety of 3 to 8 ring atoms in which one or two ring atoms are heteroatoms selected from N, O, or $S(O)_n$ (where n is an integer from 0 to 2), preferably N or O, the remaining ring atoms being C, where one or two C atoms may optionally be replaced by a carbonyl group. The heterocyclyl ring may be optionally substituted independently with one or more, preferably one, two, or three, substituents, each of which is independently selected from alkyl, haloalkyl, hydroxyalkyl, halo, nitro, cyano, cyanoalkyl, hydroxy, alkoxy, amino, mono- and dialkylamino, aralkyl, —$(X)_n$—C(O)—$R^e$ (where X is O or $NR^f$, n is 0 or 1, $R^e$ is hydrogen, alkyl, haloalkyl, hydroxy (when n is 0), alkoxy, amino, mono- and dialkylamino, or optionally substituted phenyl, and $R^f$ is H or alkyl), -alkylene-C(O)—$R^g$ (where $R^g$ is alkyl, —$OR^h$ or $NR^iR^j$ and $R^h$ is hydrogen, alkyl or haloalkyl, and $R^i$ and $R^j$ are independently hydrogen or alkyl), and —$S(O)_nR^k$ (where n is an integer from 0 to 2) such that when n is 0, $R^k$ is hydrogen, alkyl, cycloalkyl, or cycloalkylalkyl, and when n is 1 or 2, $R^k$ is alkyl, cycloalkyl, cycloalkylalkyl, amino, acylamino, monoalkylamino, or dialkylamino. A particularly preferred group of heterocyclyl substituents include alkyl, haloalkyl, hydroxyalkyl, halo, hydroxy, alkoxy, amino, mono- and dialkylamino, aralkyl, and —$S(O)_nR^k$. In particular, the term heterocyclyl includes, but is not limited to, tetrahydrofuranyl, pyridinyl, tetrahydropyranyl, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, 4-(1,1-dioxo-tetrahydro-2H-thiopyranyl), pyrrolinyl, imidazolinyl, N-methanesulfonyl-piperidin-4-yl, and the derivatives thereof, each of which may be optionally substituted.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" refers to a subset of cycloalkyl moiety as defined herein and specifically refers to a cycloalkyl moiety as defined herein where one or more, preferably one, two or three, hydrogen atoms in the cycloalkyl moiety have been replaced with a hydroxy substituent. Representative examples include, but are not limited to, 2-, 3-, or 4-hydroxycyclohexyl, and the like.

"Peptide" means an amide derived from two or more amino acids by combination of the amino group of one acid with the carboxyl group. "Monopeptide" means a single amino acid, "dipeptide" means an amide compound comprising two amino acids, "tripeptide" means an amide compound comprising three amino acids, and so on. The C-terminus of a "peptide" may be joined to another moiety via an ester functionality.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optionally substituted", when used in association with "aryl", "phenyl", "heteroaryl" "cycloalkyl" or "heterocyclyl", means an aryl, phenyl, heteroaryl, cycloalkylyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl), or as provided herein elsewhere.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The terms "pro-drug" and "prodrug" are used interchangeably herein and refer to any compound which releases an active parent drug in vivo when such prodrug is administered to a mammalian subject.

"Protecting group" refers to a grouping of atoms that when attached to a reactive group in a molecule masks, reduces or prevents that reactivity. Examples of protecting groups can be found in T. W. Green and P. G. Futs, *Protective Groups in Organic Chemistry*, (Wiley, 2$^{nd}$ ed. 1991) and Harrison and Harrison et al., *Compendium of Synthetic Organic Methods*, Vols. 1-8 (John Wiley and Sons, 1971-1996). Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

As used herein, the terms "those defined above" and "those defined herein" are used interchangeably herein and, when referring to a variable, incorporates by reference the broad definition of the variable as well as preferred, more preferred and most preferred definitions, if any.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

The terms "those defined above" and "those defined herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen. Where a chiral center is present in a structure but no specific enantiomer is shown, the structure encompasses both enantiomers associated with the chiral center.

Compounds of the Invention

U.S. patent application Ser. Nos. 11/065,890 and 11/067,336 filed on Feb. 25, 2005 and incorporated herein by reference, disclose highly effective modulators of p38 MAP kinase and are useful in the treatment of p38-mediated diseases. This invention provides prodrug compounds of these p38 modulators that achieve higher blood levels of active ingredient for more efficient dosing regimens in the treatment of p38-mediated diseases. The prodrug compounds of the invention surprisingly exhibit improved pharmacokinetic properties over the parent compounds.

Accordingly, this invention provides compounds of formula Ia, Ib, Ic, Id, Ie, If, Ig or Ih:

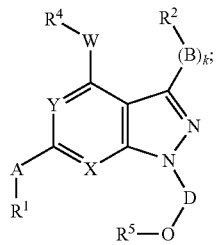
Ia

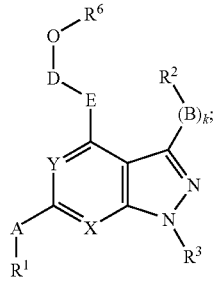
Ib

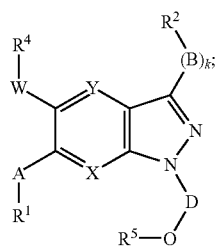
Ic

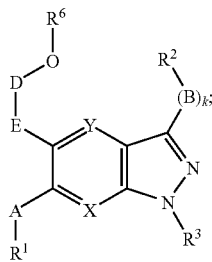
Id

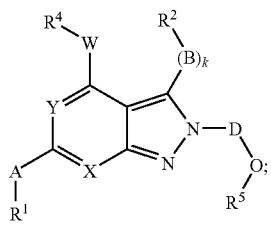
Ie

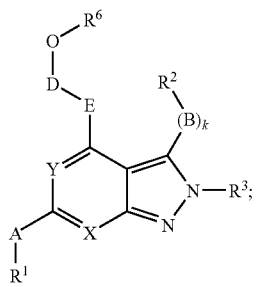
If

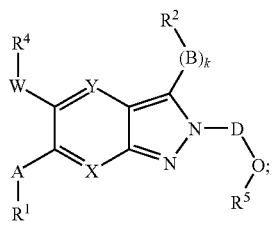
Ig

Ih or a pharmaceutically acceptable salt thereof,
wherein:
$R^1$ is aryl, heteroaryl, aralkyl or cycloalkyl;
$R^2$ is aryl, heteroaryl, cycloalkyl, branched alkyl, heterocyclyl, hydroxyalkyl, cycloalkenyl or hydroxycycloalkyl;
$R^3$ is hydrogen or alkyl;
$R^4$ is hydrogen, alkyl, hydroxy, amino, heteroalkyl, heterocyclyl, heterocyclylalkyl, hydroxycycloalkyl, cycloalkylalkyl, alkylsulfonyl, alkylsulfonamido, aryl, heteroaryl, aralkyl, heteroaralkyl, —(CHR$^a$)$_r$—C(=O)—R$^b$, —(CHR$^a$)$_r$—O—C(=O)—R$^b$, —(CHR$^a$)$_r$—NH—C(=O)—R$^b$ or —SO$_2$—R$^b$, wherein
R$^a$ is hydrogen, alkyl or heteroalkyl;
R$^b$ is alkyl, hydroxy, amino, heteroalkyl, aryl, aralkyl, heteroaryl, or heterocyclyl;
r is from 0 to 4;
R$^5$ is hydrogen, —C(=O)—R$^c$, —(O=)P(OR$^d$)$_2$, —S(=O)$_2$OR$^d$, or a mono-, di- or tri-peptide;
R$^6$ is —C(=O)—R$^c$ or —(O=)P(OR$^d$)$_2$—, —S(=O)$_2$OR$^d$, or a mono-, di- or tri-peptide;
wherein
R$^c$ is alkyl, alkoxy, amino, cycloalkyl, cycloalkylalkyl, aryl, arylalkyl, heteroaryl,
heteroarylalkyl, cycloalkyloxy, cycloalkylalkyloxy, aryloxy, arylalkyloxy, heteroaryloxy, heteroarylalkyloxy, heterocyclyl, heterocylyloxy, —(CH$_2$)$_p$—C(=O)—R$^e$, —(CH=CH)—C(=O)—R$^e$, or —CH(NH$_2$)—R$^f$;
wherein
R$^e$ is hydrogen, hydroxy, alkoxy or amino;
p is 2 or 3;
R$^f$ is hydrogen, alkyl, hydroxyalkyl, aminoalkyl, optionally substituted phenyl, benzyl, guanidinylalkyl, carboxyalkyl, amidoalkyl, thioalkyl or imidazolalkyl;
R$^d$ is hydrogen, alkyl, an alkalai metal ion or an alkaline earth metal ion;
X and Y are nitrogen, or one of X and Y is nitrogen and the other is CR$^g$;
wherein
R$^g$ is hydrogen, alkyl, hydroxy, alkoxy, amino, haloalkyl, cyano, halo, heteroalkyl, C(=O)—R$^h$ or —SO$_2$—R$^h$,
wherein
R$^h$ is hydrogen or alkyl;
D is —(CR$^7$R$^8$)$_n$—;
wherein
n is from 1 to 3;
R$^7$ and R$^8$ each independently is hydrogen or alkyl;
W is a bond, O, S(O)$_q$, CH$_2$ or NR$^i$;
E is O, S(O)$_q$, CH$_2$ or NR$^i$;
wherein
q is from 0 to 2;
R$^i$ is hydrogen, alkyl, heteroalkyl, heterocyclyl, hydroxycycloalkyl,
—C(=O)—R$^j$ or —SO$_2$—R$^j$,
wherein
R$^j$ is alkyl, aryl, aralkyl, heteroaryl, heteroalkyl or heterocyclyl;
or R$^4$ and R$^i$ together with the atoms to which they are attached may form a heterocyclic ring;
A is O, CH$_2$, S(O)$_s$, C(=O), NR$^k$, or CH(OR$^k$),
wherein
s is from 0 to 2;
R$^k$ is hydrogen or alkyl,
k is 0 or 1;
B is O, S(O)$_j$, —(CHR$^m$)$_t$, —NR$^m$SO$_2$—, NR$^m$, NR$^m$C(=O) or C(=O),
wherein
j is 0, 1 or 2;
t is from 1 to 3; and
R$^m$ is hydrogen or alkyl.
In certain embodiments of any of formulas Ia through Ih, k is 0.
In certain embodiments of any of formulas Ia through Ih, X and Y are nitrogen.
In certain embodiments of any of formulas Ia through Ih, A is O, S or NR$^h$.

In certain embodiments of any of formulas Ia through Ih, R$^2$ is aryl.
In certain embodiments of any of formulas Ia through Ih, R$^1$ is aryl.
In certain embodiments of any of formulas Ia through Ih, R$^2$ is optionally substituted phenyl, such as 2-halophenyl, 2,4-dihalophenyl, or 2-halo-5-alkylsulfonylphenyl.
In certain embodiments of any of formulas Ia through Ih, R$^1$ is optionally substituted phenyl, such as phenyl substituted once or twice with halo. In specific embodiments R$^1$ may be 2,4-dihalophenyl such as 2,4-fluorophenyl.
In certain embodiments of any of formulas Ia through Ih, X is nitrogen and Y is CR$^g$.
In certain embodiments of any of formulas Ia through Ih, Y is nitrogen and X is CR$^g$.
In certain embodiments of any of formulas Ia through Ih, A is O.
In certain embodiments of any of formulas Ia through Ih, n is 1 or 2.
In certain embodiments of any of formulas Ia through Ih, R$^7$ and R$^8$ are hydrogen.
In certain embodiments of any of formulas Ia through Ih, R$^2$ is phenyl substituted once or twice with halo, alkyl, haloalkyl, cyano, heteroalkyl, heterocyclyl, alkylsulfonyl, aminosulfonyl, hydroxycycloalkyl, heteroaryl, heterocyclylalkyl, heterocyclyloxy, heterocyclylalkoxy, heteroarylalkyl, heteroaryloxy, heteroarylalkoxy, or —C(=O)—R$^n$,
wherein
R$^n$ is alkyl, haloalkyl, heteroalkyl, heterocyclyl, cycloalkyl, cycloalkylalkyl, heterocyclkylalkyl, aryl, arylalkyl, heteroaryl or heteroarylalkyl.
In certain embodiments of any of formulas Ia through Ih, R$^2$ is heteroaryl. Preferred heteroaryl include thienyl, furanyl, pyridinyl and pyrimidinyl.
In certain embodiments of any of formulas Ia through Ih, k is 0, A is O and X and Y are nitrogen.
In certain embodiments of any of formulas Ia through Ih, k is 0, A is O, X and Y are nitrogen and R$^1$ is optionally substituted phenyl.
In certain embodiments of any of formulas Ia through Ih, k is 0, A is O, X and Y are nitrogen, R$^1$ is optionally substituted phenyl and R$^2$ is optionally substituted phenyl.
In certain embodiments of any of formulas Ia, Ic, Ie and Ig, k is 0, A is O, X and Y are nitrogen, R$^1$ is optionally substituted phenyl, R$^2$ is optionally substituted phenyl and n is 1.
In certain embodiments of any of formulas Ia, Ic, Ie and Ig, k is 0, A is O, X and Y are nitrogen, R$^1$ is optionally substituted phenyl, R$^2$ is optionally substituted phenyl, n is 1 and R$^7$ and R$^8$ are hydrogen.
In certain embodiments of any of formulas Ia, Ic, Ie and Ig, W is O or NR$^i$. In many such embodiments W is NR$^i$.
In certain embodiments of any of formulas Ia, Ic, Ie and Ig, R$^4$ is heteroalkyl. Exemplary heteroalkyl include hydroxyalkyl, aminoalkyl, alkoxyalkyl and alkylsulfonylalkyl. Preferred heteroalkyl are hydroxyalkyl, alkoxyalkyl and alkylsulfonylalkyl, and more preferred are hydroxyalkyl and alkylsulfonylalkyl.
In certain embodiments of any of formulas Ia, Ic, Ie and Ig, R$^5$ is hydrogen.
In certain embodiments of any of formulas Ia, Ic, Ie and Ig, R$^5$ is —C(=O)—R$^c$.
In certain embodiments of any of formulas Ia, Ic, Ie and Ig, R$^c$ is —(CH$_2$)$_p$—C(=O)—R$^e$. In such embodiments p may be 2 and R$^e$ may be hydroxy.
In certain embodiments of any of formulas Ia, Ic, Ie and Ig, R$^5$ is —(O=)P(OR$^d$)$_2$—. In such embodiments R$^d$ may be hydrogen.

In certain embodiments of any of formulas Ia, Ic, Ie and Ig, $R^c$ is —CH(NH$_2$)—$R^f$. In such embodiments $R^f$ may be alkyl.

In certain embodiments of any of formulas Ia, Ic, Ie and Ig, k is 0, W is a bond and $R^4$ is hydrogen.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, and $R^4$ is heteroalkyl, preferably hydroxyalkyl or alkylsulfonyllalkyl.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, $R^4$ is hydroxyalkyl or alkylsulfonylalkyl, and $R^5$ is hydrogen.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, $R^4$ is hydroxyalkyl or alkylsulfonylalkyl, and $R^5$ is —C(═O)—$R^c$.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, $R^4$ is hydroxyalkyl or alkylsulfonylalkyl, $R^5$ is —C(═O)—$R^c$, and $R^c$ is —(CH$_2$)$_p$—C(═O)—$R^e$. In such embodiments p may be 2 and $R^e$ may be hydroxy.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, $R^4$ is hydroxyalkyl or alkylsulfonylalkyl, $R^5$ is —C(═O)—$R^c$, and $R^c$ is —CH(NH$_2$)—$R^f$. In such embodiments $R^f$ may be alkyl.

In certain embodiments of any of formulas Ia, Ic, Ie and Ig, k is 0, A is O, X and Y are nitrogen, $R^1$ is optionally substituted phenyl, $R^2$ is optionally substituted phenyl, n is 1, $R^7$ and $R^8$ are hydrogen, W is NR$^i$, $R^4$ is hydroxyalkyl or alkylsulfonylalkyl, and $R^5$ is —(O═)P(OR$^d$)$_2$—. In such embodiments Rd may be hydrogen.

In certain embodiments of any of formulas Ib, Id, If and Ih, k is 0, A is O, X and Y are nitrogen, $R^1$ is optionally substituted phenyl, $R^2$ is optionally substituted phenyl and n is 2.

In certain embodiments of any of formulas Ib, Id, If and Ih, E is O or NR$^i$. In many such embodiments E is NR$^i$.

In certain embodiments of any of formulas Ib, Id, If and Ih, $R^6$ is hydrogen.

In certain embodiments of any of formulas Ib, Id, If and Ih, $R^6$ is —C(═O)—$R^c$.

In certain embodiments of any of formulas Ib, Id, If and Ih, $R^c$ is —(CH$_2$)$_p$—C(═)—$R^e$. In such embodiments p may be 2 and $R^e$ may be hydroxy.

In certain embodiments of any of formulas Ib, Id, If and Ih, $R^6$ is —(O═)P(OR$^d$)$_2$—. In such embodiments $R^d$ may be hydrogen.

In certain embodiments of any of formulas Ib, Id, If and Ih, $R^c$ is —CH(NH$_2$)—$R^f$. In such embodiments $R^f$ may be alkyl.

In certain embodiments of any of formulas Ib, Id, If and Ih, k is 0, A is O, X and Y are nitrogen, $R^1$ is optionally substituted phenyl, $R^2$ is optionally substituted phenyl, n is 2 and E is NR$^i$.

In certain embodiments of any of formulas Ib, Id, If and Ih, k is 0, A is O, X and Y are nitrogen, $R^1$ is optionally substituted phenyl, $R^2$ is optionally substituted phenyl, n is 2, E is NR$^i$, and $R^f$ is —C(═O)—$R^c$.

In certain embodiments of any of formulas Ib, Id, If and Ih, k is 0, A is O, X and Y are nitrogen, $R^1$ is optionally substituted phenyl, $R^2$ is optionally substituted phenyl, n is 2, E is NR$^i$, $R^6$ is —C(═O)—$R^c$, and $R^c$ is —(CH$_2$)$_p$—C(═O)—$R^e$. In such embodiments p may be 2 and $R^e$ may be hydroxy.

In certain embodiments of any of formulas Ib, Id, If and Ih, k is 0, A is O, X and Y are nitrogen, $R^1$ is optionally substituted phenyl, $R^2$ is optionally substituted phenyl, n is 2, E is NR$^i$, $R^6$ is —C(═O)—$R^c$, and $R^c$ is —CH(NH$_2$)—$R^f$. In such embodiments $R^f$ may be alkyl.

In certain embodiments of any of formulas Ib, Id, If and Ih, k is 0, A is O, X and Y are nitrogen, $R^1$ is optionally substituted phenyl, $R^2$ is optionally substituted phenyl, n is 2, E is NR$^i$, and $R^6$ is —(O═)P(OR$^d$)$_2$—. In such embodiments $R^d$ may be hydrogen.

In certain embodiments of the invention the subject compounds may be of the formula IIa, IIb, IIc, IId, IIe, IIf, IIg or IIh;

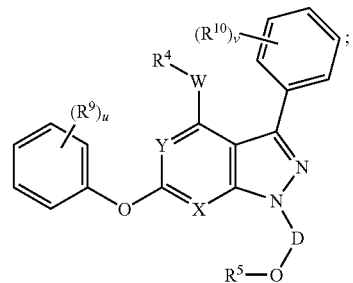

IIa

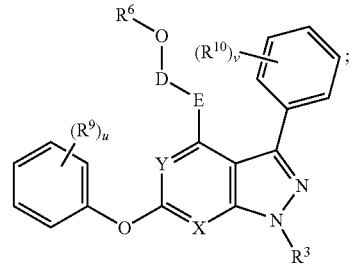

IIb

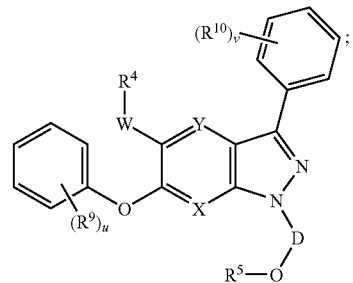

IIc

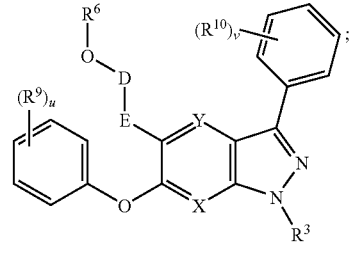

IId

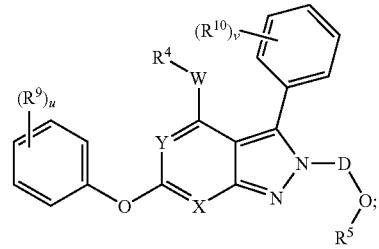

IIe

-continued

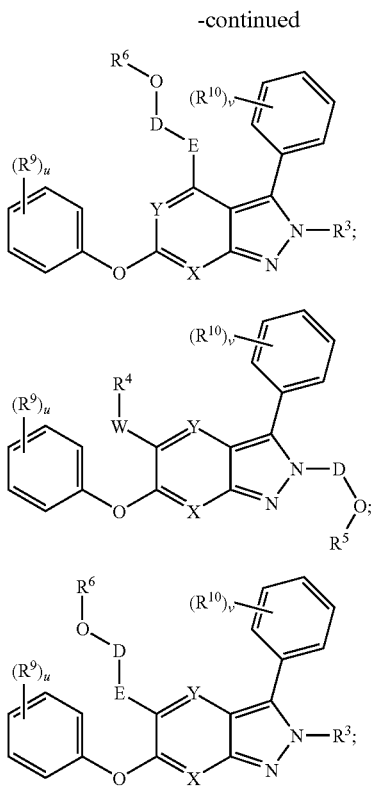

IIf

IIg

IIh wherein
u is from 0 to 4;
v is from 0 to 4;
each $R^9$ is independently halo, alkyl, alkoxy, haloalkyl, or cyano;
each $R^{10}$ is independently halo, alkyl, haloalkyl, cyano, heteroalkyl, heterocyclyl, alkylsulfonyl, aminosulfonyl, hydroxycycloalkyl, heteroaryl, heterocyclylalkyl, heterocyclyloxy, heterocyclylalkoxy, heteroarylalkyl, heteroaryloxy, heteroarylalkoxy, or —C(=O)—R", 
wherein
R" is alkyl, haloalkyl, heteroalkyl, heterocyclyl, cycloalkyl, cycloalkylalkyl, heterocyclylalkyl, aryl, arylalkyl, heteroaryl or heteroarylalkyl; and
W, X, Y, D, B, $R^4$, $R^5$ and $R^6$ are as defined herein.

In certain embodiments of any formulas IIa through IIf, u is 1 or 2 and $R^9$ is halo. Preferably u is 2 and $R^9$ is fluoro.

In certain embodiments of any formulas IIa through IIf, v is 1 or 2 and $R^{10}$ is halo or alkylsulfonyl. In such embodiments v may be 1 and $R^{10}$ may be chloro, or v may be 2 and each $R^{10}$ may be fluoro, or v may be 2 and one of $R^{10}$ is halo and the other is alkylsulfonyl.

In certain embodiments of any of formulas IIa, IIc, IIe or IIg, n is 1.

In certain embodiments of any formulas IIa, IIc, IIe or IIg, $R^7$ and $R^8$ are hydrogen.

In certain embodiments of any formulas IIa, IIc, IIe or IIg, W is O or $NR^i$. Preferably W is $NR^i$.

In certain embodiments of any formulas IIa, IIc, IIe or IIg, W is a bond and $R^4$ is hydrogen.

In certain embodiments of any formulas IIa, IIc, IIe or IIg, $R^4$ is heteroalkyl. Exemplary heteroalkyl include hydroxyalkyl, aminoalkyl, alkoxyalkyl and alkylsulfonylalkyl. Preferred heteroalkyl are hydroxyalkyl, alkoxyalkyl and alkylsulfonylalkyl, and more preferred are hydroxyalkyl and alkylsulfonylalkyl.

In certain embodiments of any formulas IIa, IIc, IIe or IIg, $R^5$ is hydrogen.

In certain embodiments of any formulas IIa, IIc, IIe or IIg, $R^5$ is —C(=O)—$R^c$.

In certain embodiments of any of IIa, IIc, IIe or IIg, $R^c$ is —(CH$_2$)$_p$—C(=O)—$R^e$. In such embodiments p may be 2 and $R^e$ may be hydroxy.

In certain embodiments of any of formulas IIa, IIc, IIe or IIg, $R^5$ is —(O=)P(OR$^d$)$_2$—. In such embodiments $R^d$ may be hydrogen.

In certain embodiments of any formulas IIa, IIc, IIe or IIg, $R^c$ is —CH(NH$_2$)—$R^f$. In such embodiments $R^f$ may be alkyl.

In certain embodiments of any formulas IIa, IIc, IIe or IIg, n is 1 and $R^7$ and $R^8$ are hydrogen.

In certain embodiments of any formulas IIa, IIc, IIe or IIg, n is 1, $R^7$ and $R^8$ are hydrogen, u is 2 and $R^9$ is fluoro.

In certain embodiments of any formulas IIa through IIf, n is 1, $R^7$ and $R^8$ are hydrogen, u is 2, $R^9$ is fluoro, and v is 1 and $R^{10}$ is chloro or v is 2 and each $R^{10}$ is independently halo or alkylsulfonyl.

In certain embodiments of any formulas IIa, IIc, IIe or IIg, n is 1, $R^7$ and $R^8$ are hydrogen, u is 2, $R^9$ is fluoro, v is 1, $R^{10}$ is chloro and W is $NR^i$.

In certain embodiments of any formulas IIa, IIc, IIe or IIg, n is 1, $R^7$ and $R^8$ are hydrogen, u is 2, $R^9$ is fluoro, v is 1 and $R^{10}$ is chloro or v is 2 and each $R^{10}$ is independently halo or alkylsulfonyl, W is $NR^i$ and $R^4$ is hydroxyalkyl or alkylsulfonylalkyl.

In certain embodiments of any formulas IIa, IIc, IIe or IIg, n is 1, $R^7$ and $R^8$ are hydrogen, u is 2, $R^9$ is fluoro, v is 1 and $R^{10}$ is chloro or v is 2 and each $R^{10}$ is independently halo or alkylsulfonyl, W is $NR^i$, $R^4$ is hydroxyalkyl or alkylsulfonylalkyl and $R^5$ is hydrogen.

In certain embodiments of any formulas IIa, IIc, IIe or IIg, n is 1, $R^7$ and $R^8$ are hydrogen, u is 2, $R^9$ is fluoro, v is 1, $R^{10}$ is chloro, W is $NR^i$, $R^4$ is hydroxyalkyl or alkylsulfonylalkyl and $R^5$ is —C(=O)—$R^c$.

In certain embodiments of any formulas IIa, IIc, IIe or IIg, n is 1, $R^7$ and $R^8$ are hydrogen, u is 2, $R^9$ is fluoro, v is 1 and $R^{10}$ is chloro or v is 2 and each $R^{10}$ is independently halo or alkylsulfonyl, W is $NR^i$, $R^4$ is hydroxyalkyl or alkylsulfonylalkyl, $R^5$ is —C(=O)—$R^c$, and $R^c$ is —(CH$_2$)$_p$—C(=O)—$R^e$. In such embodiments p may be 2 and $R^e$ may be hydroxy.

In certain embodiments of any formulas IIa, IIc, IIe or IIg, n is 1, $R^7$ and $R^8$ are hydrogen, u is 2, $R^9$ is fluoro, v is 1 and $R^{10}$ is chloro or v is 2 and each $R^{10}$ is independently halo or alkylsulfonyl, W is $NR^i$, $R^4$ is hydroxyalkyl or alkylsulfonylalkyl, $R^5$ is —C(=O)—$R^c$, and $R^c$ is —CH(NH$_2$)—$R^f$. In such embodiments $R^f$ may be alkyl.

In certain embodiments of any formulas IIa, IIc, IIe or IIg, n is 1, $R^7$ and $R^8$ are hydrogen, u is 2, $R^9$ is fluoro, v is 1 and $R^{10}$ is chloro or v is 2 and each $R^{10}$ is independently halo or alkylsulfonyl, W is $NR^i$, $R^4$ is hydroxyalkyl or alkylsulfonylalkyl and $R^5$ is —(O=)P(OR$^d$)$_2$—. In such embodiments $R^d$ may be hydrogen.

In certain embodiments of any of formulas IIb, IId, IIf or IIh, n is 2.

In certain embodiments of any formulas IIb, IId, IIf or IIh, E is O or $NR^i$. Preferably E is $NR^i$.

In certain embodiments of any formulas IIb, IId, IIf or IIh, $R^6$ is hydrogen.

In certain embodiments of any formulas IIb, IId, IIf or IIh, $R^6$ is —C(=O)—$R^c$.

In certain embodiments of any of IIb, IId, IIf or IIh, $R^c$ is —(CH$_2$)$_p$—C(=O)—$R^e$. In such embodiments p may be 2 and $R^e$ may be hydroxy.

In certain embodiments of any of formulas IIa, IIc, IIe or IIg, $R^5$ is —(O=)P(OR$^d$)$_2$—. In such embodiments $R^d$ may be hydrogen.

In certain embodiments of any formulas IIb, IId, IIf or IIh, $R^c$ is —CH(NH$_2$)—$R^f$. In such embodiments $R^f$ may be alkyl.

In certain embodiments of any formulas IIb, IId, IIf or IIh, n is 2, u is 2 and $R^9$ is fluoro.

In certain embodiments of any formulas IIb, IId, IIf or IIh, n is 2, u is 2, $R^9$ is fluoro, and v is 1 and $R^{10}$ is chloro or v is 2 and each $R^{10}$ is independently halo or alkylsulfonyl.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, and E is NR$^i$.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, E is NR$^i$ and $R^6$ is hydrogen.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, E is NR$^i$ and $R^6$ is —C(=O)—$R^c$.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, E is NR$^i$, $R^6$ is —C(=O)—$R^c$, and $R^c$ is —(CH$_2$)$_p$—C(=O)—$R^e$. In such embodiments p may be 2 and $R^e$ may be hydroxy.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, E is NR$^i$, $R^6$ is —C(=O)—$R^c$, and $R^c$ is —CH(NH$_2$)—$R^f$. In such embodiments $R^f$ may be alkyl.

In certain embodiments of any formulas IIb, IId, IIf or IIh, n is 2, u is 2, $R^9$ is fluoro, v is 1 and $R^{10}$ is chloro or v is 2 and each $R^{10}$ is independently halo or alkylsulfonyl, E is NR$^i$ and $R^6$ is —(O=)P(OR$^d$)$_2$—. In such embodiments $R^d$ may be hydrogen.

In certain embodiments of the invention the subject compounds may be of the formula IIb.

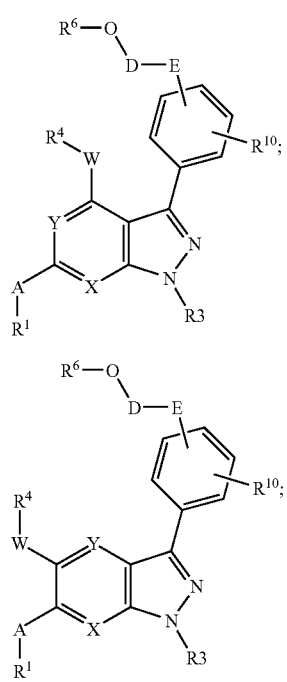

IIIa

IIIb wherein A, D, E, W, X, Y, $R^1$, $R^3$, $R^4$ and $R^{10}$, are as defined herein.

In certain embodiments of the invention the subject compounds may be of the formula IVa or IVb:

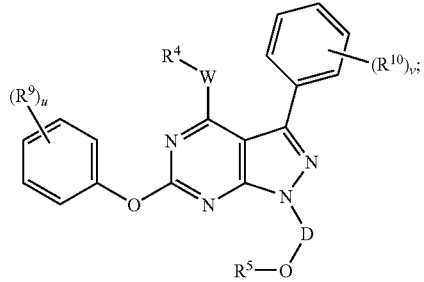

IVa

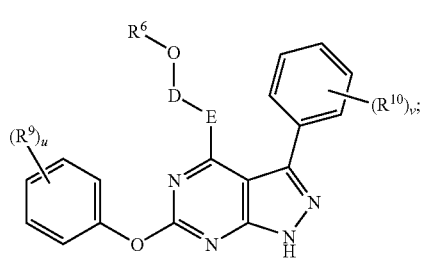

IVb wherein u, v, D, E, W, $R^4$, $R^5$, $R^6$, $R^9$ and $R^{10}$ are as defined herein.

In certain embodiments of formula IVa, W is a bond and $R^4$ is hydrogen.

In certain embodiments of formula IVa, W is O or NR$^1$ and $R^4$ is hydroxyalkyl or alkylsulfonylalkyl.

In certain embodiments of formula IVa, n is 1 and $R^7$ and $R^8$ are hydrogen.

In certain embodiments of formula IVa, u is 1 or 2 and $R^9$ is halo. Preferably u is 2 and $R^9$ is fluoro.

In certain embodiments of formula IVa, v is 1 or 2 and each $R^{10}$ is independently halo or alkylsulfonyl.

In certain embodiments of formula IVa, $R^5$ is hydrogen.

In certain embodiments of formula IVa, $R^5$ is —C(=O)—$R^c$.

In certain embodiments of formula IVa, $R^c$ is —(CH$_2$)$_p$—C(=O)—$R^e$. In such embodiments p may be 2 and $R^e$ may be hydroxy.

In certain embodiments of formula IVa, $R^5$ is —(O=)P(OR$^d$)$_2$—. In such embodiments $R^d$ may be hydrogen.

In certain embodiments of formula IVa, $R^c$ is —CH(NH$_2$)—$R^f$. In such embodiments $R^f$ may be alkyl.

In certain embodiments of formula IVa, n is 1, $R^7$ and $R^8$ are hydrogen, u is 1 or 2 and $R^9$ is halo, v is 1 or 2, each $R^{10}$ is independently halo or alkylsulfonyl, W is a bond and $R^4$ is hydrogen.

In certain embodiments of formula IVa, n is 1, $R^7$ and $R^8$ are hydrogen, u is 1 or 2 and $R^9$ is halo, v is 1 or 2, each $R^{10}$ is independently halo or alkylsulfonyl, W is O or NR$^i$ and $R^4$ is hydroxyalkyl or alkylsulfonylalkyl.

In certain embodiments of formula IVb, n is 2 and $R^7$ and $R^8$ each independently is hydrogen or methyl.

In certain embodiments of formula IVb, u is 1 or 2 and $R^9$ is halo. Preferably u is 2 and $R^9$ is fluoro.

In certain embodiments of formula IVb, v is 1 or 2 and each $R^{10}$ is independently halo or alkylsulfonyl.

In certain embodiments of formula IVb, $R^6$ is hydrogen.

In certain embodiments of formula IVa, $R^6$ is —C(=O)—$R^c$.

In certain embodiments of formula IVa, $R^c$ is —(CH$_2$)$_p$—C(=O)—$R^e$. In such embodiments p may be 2 and $R^e$ may be hydroxy.

In certain embodiments of formula IVa, $R^6$ is —(O=)P$(OR^d)_2$—. In such embodiments $R^d$ may be hydrogen.

In certain embodiments of formula IVa, $R^e$ is —CH$(NH_2)$—$R^f$. In such embodiments $R^f$ may be alkyl.

In certain embodiments of formula IVb, n is 2, $R^7$ and $R^8$ each independently is hydrogen or methyl, u is 1 or 2 and $R^9$ is halo, v is 1 or 2 and each $R^{10}$ is independently halo or alkylsulfonyl, and E is O or $NR^i$.

In embodiments of the invention where any of $R^1$, $R^2$, $R^3$, $R^4$, $R^5$, $R^6$, $R^7$, $R^8$, $R^9$, $R^{10}$, $R^a$, $R^b$, $R^c$, $R^d$, $R^e$, $R^f$, $R^g$, $R^h$, $R^i$, $R^j$, $R^k$ or $R^m$ is alkyl or contains an alkyl moiety, such alkyl is preferably lower alkyl, i.e. $C_1$-$C_6$alkyl, and more preferably $C_1$-$C_4$alkyl.

Pharmaceutically acceptable acid addition salts of the compounds of Formula I include salts derived from inorganic acids such as hydrochloric, nitric, phosphoric, sulfuric, hydrobromic, hydriodic, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science*, 1977, 66, 1-19).

The acid addition salts of the basic compounds can be prepared by contacting the free base form with a sufficient amount of the desired acid to produce the salt in the conventional manner. The free base form can be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Representative compounds in accordance with the invention are shown below in Table 1.

TABLE 1

| # | Structure | Name (Autonom ™) | MP/M + H |
|---|---|---|---|
| 1 | 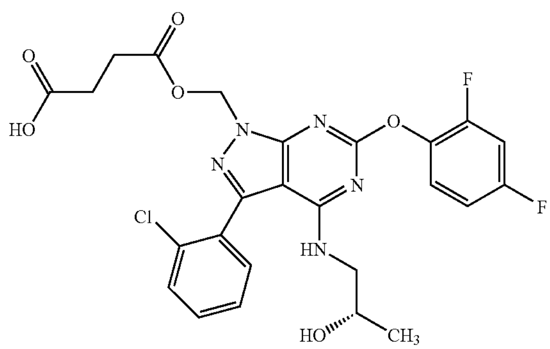 | Succinic acid mono-[3-(2-chloro-phenyl)-6-(2,4-difluoro-phenoxy)-4-(2-hydroxy-propylamino)-pyrazolo[3,4-d]pyrimidin-1-ylmethyl]ester | 562 |
| 2 | 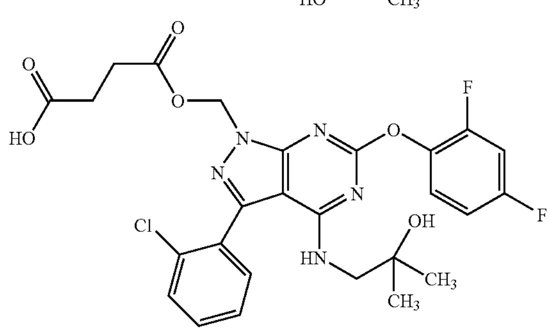 | Succinic acid mono-[3-(2-chloro-phenyl)-6-(2,4-difluoro-phenoxy)-4-(2-hydroxy-2-methyl-propylamino)-pyrazolo[3,4-d]pyrimidin-1-ylmethyl]ester | 576 |
| 3 | 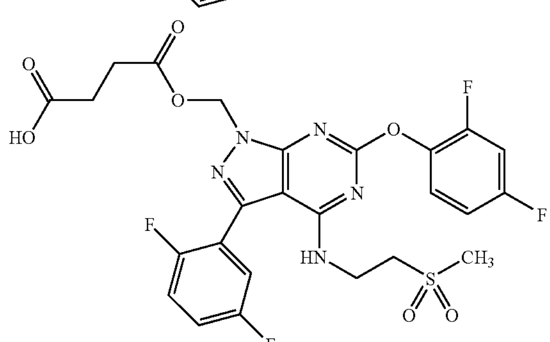 | Succinic acid mono-[3-(2-chloro-phenyl)-6-(2,4-difluoro-phenoxy)-4-(2-methanesulfonyl-ethylamino)-pyrazolo[3,4-d]pyrimidin-1-ylmethyl]ester | 612 |

TABLE 1-continued

| # | Structure | Name (Autonom ™) | MP/M + H |
|---|-----------|------------------|----------|
| 4 | 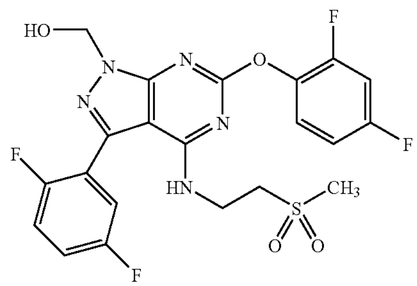 | [3-(2-Chloro-phenyl)-6-(2,4-difluoro-phenoxy)-4-(2-methanesulfonyl-ethylamino)-pyrazolo[3,4-d]pyrimidin-1-yl]-methanol | — |
| 5 | 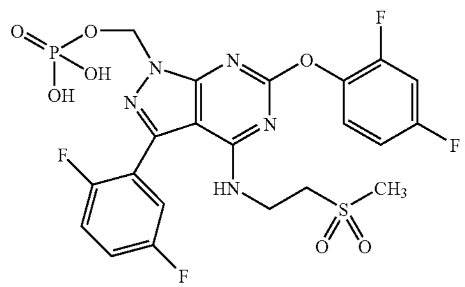 | Phosphoric acid mono-[3-(2-chloro-phenyl)-6-(2,4-difluoro-phenoxy)-4-(2-methanesulfonyl-ethylamino)-pyrazolo[3,4-d]pyrimidin-1-ylmethyl]ester | 590 (M − H) |
| 6 | 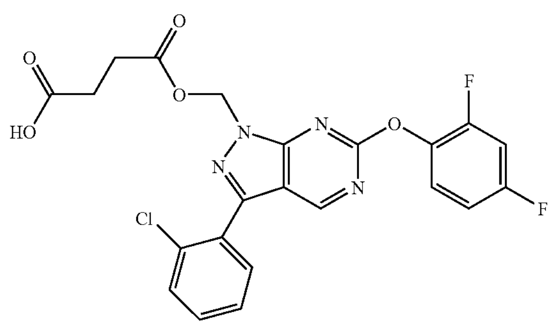 | Succinic acid mono-[3-(2-chloro-phenyl)-6-(2,4-difluoro-phenoxy)-pyrazolo[3,4-d]pyrimidin-1-ylmethyl]ester | 489 |
| 7 | 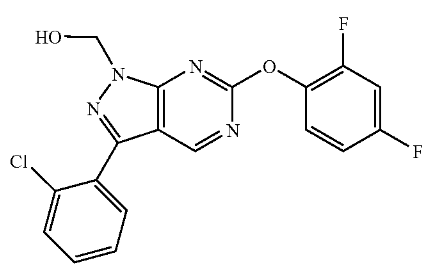 | [3-(2-Chloro-phenyl)-6-(2,4-difluoro-phenoxy)-pyrazolo[3,4-d]pyrimidin-1-yl]-methanol | — |
| 8 | 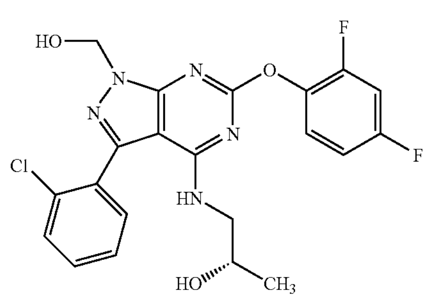 | 1-[3-(2-Chloro-phenyl)-6-(2,4-difluoro-phenoxy)-1-hydroxymethyl-1H-pyrazolo[3,4-d]pyrimidin-4-ylamino]-propan-2-ol | 462 |

TABLE 1-continued

| # | Structure | Name (Autonom ™) | MP/M + H |
|---|---|---|---|
| 9 | 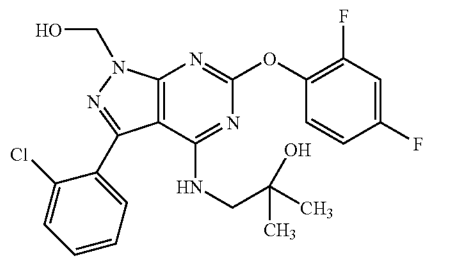 | 1-[3-(2-Chloro-phenyl)-6-(2,4-difluoro-phenoxy)-1-hydroxymethyl-1H-pyrazolo[3,4-d]pyrimidin-4-ylamino]-2-methyl-propan-2-ol | 476 |
| 10 | 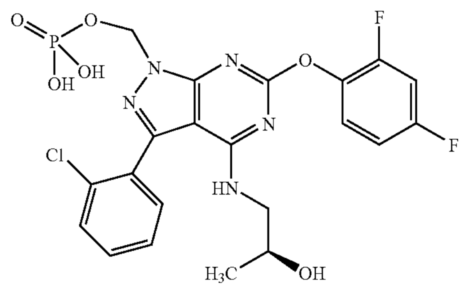 | Phosphoric acid mono-[3-(2-chloro-phenyl)-6-(2,4-difluoro-phenoxy)-4-(2-hydroxy-propylamino)-pyrazolo[3,4-d]pyrimidin-1-ylmethyl]ester | 542 |
| 11 | 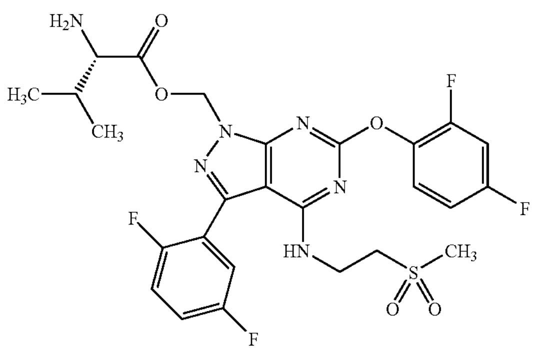 | 2-Amino-3-methyl-butyric acid 3-(2-chloro-phenyl)-6-(2,4-difluoro-phenoxy)-4-(2-methanesulfonyl-ethylamino)-pyrazolo[3,4-d]pyrimidin-1-ylmethyl ester | 611 |
| 12 | 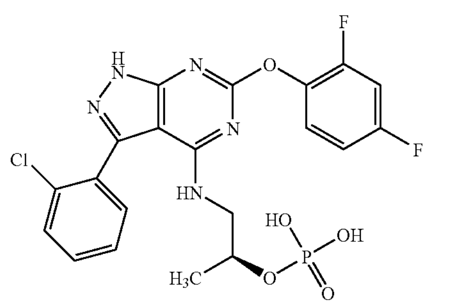 | Phosphoric acid mono-{2-[3-(2-chloro-phenyl)-6-(2,4-difluoro-phenoxy)-1H-pyrazolo[3,4-d]pyrimidin-4-ylamino]-1-methyl-ethyl} ester | |
| 13 | 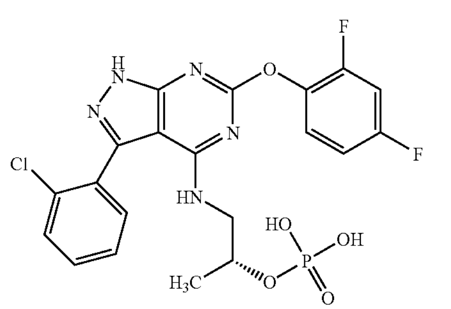 | Phosphoric acid mono-{2-[3-(2-chloro-phenyl)-6-(2,4-difluoro-phenoxy)-1H-pyrazolo[3,4-d]pyrimidin-4-ylamino]-1-methyl-ethyl} ester | |

TABLE 1-continued

| # | Structure | Name (Autonom ™) | MP/M + H |
|---|-----------|------------------|----------|
| 14 | 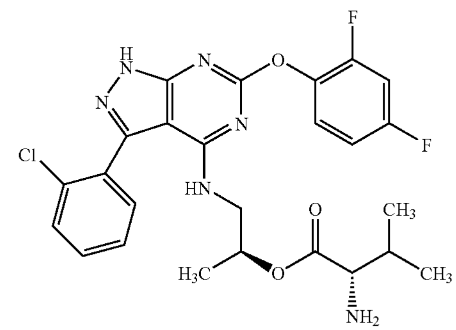 | 2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester | |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

One of the specific methods for preparing pyrazolopyrimidine compounds of the invention is shown in Scheme I below, wherein X, Y, A, u, v, $R^4$, $R^9$, $R^{10}$, $R^c$, $R^d$ and $R^i$ are as described herein.

Scheme I

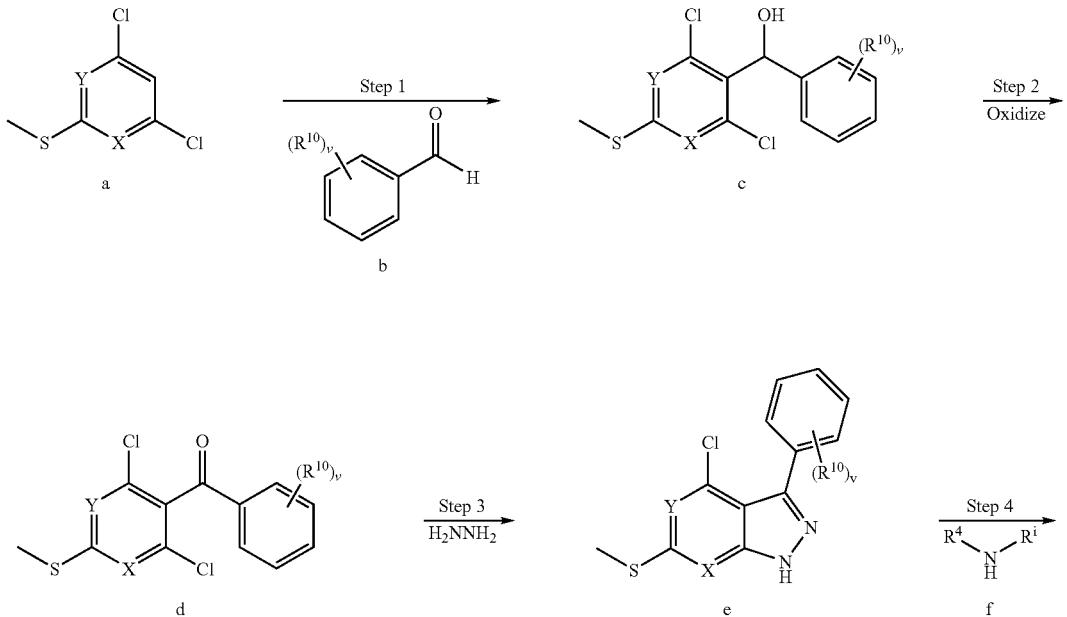

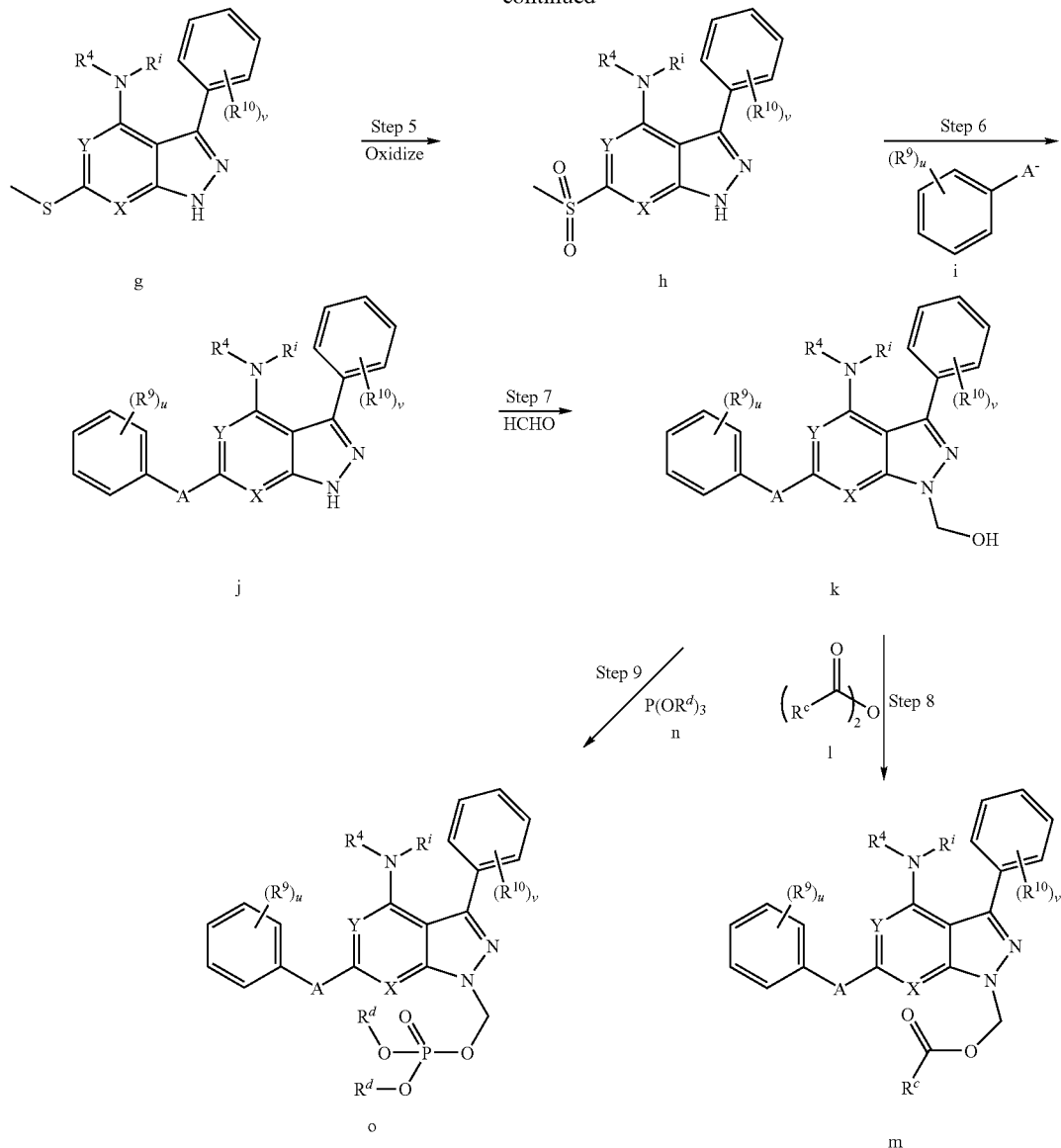

In step 1 of Scheme I, a dichlorothio compound a is deprotonated using a base, such as lithium diisopropylamide (LDA) or other suitable bases that are well known to one skilled in the art. The deprotonated pyrimidine a is reacted with a benzaldehyde b or its derivative to produce an alcohol c. This alcohol c is oxidized in step 2, e.g., by manganese oxide or the like, to produce a pyrimidine phenyl ketone d. Reacting the ketone d with hydrazine in step 3 affords a ring closure product in the form of a pyrazolopyrimidine e. Reaction of pyrazolopyrimidine e in step 4 with a nucleophile such as amine f displaces the chloro group on compound e to afford an amino compound f. Alternatively, an alkoxide $R^4O^-$ or thioalkoxide $R^4S^-$ may be used in place of amine f. In step 5 the thio group on compound f may then be oxidized, e.g., with Oxone, meta-chloroperbenzoic acid, or other oxidizing agents known to one skilled in the art, to produce a sulfonyl derivative g. The sulfonyl group on compound g is then displaced in step 6 with a nucleophilic aryl group h, such as an optionally substituted phenoxide, optionally substituted aniline, or an optionally substituted thiophenoxide, to produce compound j. In step 7, the 1-position nitrogen of compound j is alkylated by reaction with formaldehyde to yield hydroxymethyl compound k. Compound k may then be treated with an anhydride l to afford ester compound m. Anhydride may be cyclic anhydride such as maleic or succinic anhydride. Compound o may optionally be hydrolized so that $R^d$ is hydrogen. Compounds m and o are compounds of formula Ia in accordance with the invention.

One of skill in the art will understand that certain modifications to the above schemes are contemplated and within the scope of the present invention. For example, certain steps will involve the use of protecting groups for functional groups that are not compatible with particular reaction conditions.

Additional synthetic procedures useful for making compounds of the invention, including various combinations of aza substitutions for X and Y, are disclosed in U.S. patent application Ser. Nos. 11/065,890 and 11/067,336 filed on Feb. 25, 2005, the disclosures of which are incorporated herein by reference.

More specific details for producing compounds of the invention are described in the Examples section below.

Pharmaceutical Compositions And Administration

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease. The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in the Examples below.

Utility

Compounds of the invention are useful for, but not limited to, the treatment of any disorder or disease state in a human, or other mammal, which is exacerbated or caused by excessive or unregulated TNF or p38 kinase production by such mammal. Accordingly, the present invention provides a method of treating a p38-mediated disease which comprises administering an effective amount of a compound of the invention, or a pharmaceutically acceptable salt, solvate or prodrug thereof, to a subject or patient in need thereof.

Compounds of the invention are useful for, but not limited to, the treatment of inflammation in a subject, and for use as antipyretics for the treatment of fever. Compounds of the invention would be useful to treat arthritis, including but not limited to, rheumatoid arthritis, spondyloarthropathies, gouty arthritis, osteoarthritis, systemic lupus erythematosus and juvenile arthritis, osteoarthritis, gouty arthritis and other arthritic conditions. Such compounds would be useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of viral and bacterial infections, including sepsis, septic shock, gram negative sepsis, malaria, meningitis, cachexia secondary to infection or malignancy, cachexia secondary to acquired immune deficiency syndrome (AIDS), AIDS, ARC (AIDS related complex), pneumonia, and herpes virus. The compounds are also useful for the treatment of bone resorption diseases, such as osteoporosis, endotoxic shock, toxic shock syndrome, reperfusion injury, autoimmune disease including graft vs. host reaction and allograft rejections, cardiovascular diseases including atherosclerosis, thrombosis, congestive heart failure, and cardiac reperfusion injury, renal reperfusion injury, liver disease and nephritis, and myalgias due to infection.

The compounds are also useful for the treatment of Alzheimer's disease, influenza, multiple sclerosis, cancer, diabetes, systemic lupus erthrematosis (SLE), skin-related conditions such as psoriasis, eczema, burns, dermatitis, keloid formation, and scar tissue formation. In addition, compounds of the invention are useful in treating gastrointestinal conditions such as inflammatory bowel disease, Crohn's disease, gastritis, irritable bowel syndrome and ulcerative colitis. The compounds are also useful in the treatment of ophthalmic diseases, such as retinitis, retinopathies, uveitis, ocular photophobia, and of acute injury to the eye tissue. The compounds can also be used in treating angiogenesis, including neoplasia; metastasis; ophthalmological conditions such as corneal graft rejection, ocular neovascularization, retinal neovascularization including neovascularization following injury or infection, diabetic retinopathy, retrolental fibroplasia and neovascular glaucoma; ulcerative diseases such as gastric ulcer; pathological, but non-malignant, conditions such as hemangiomas, including infantile hemangiomas, angiofibroma of the nasopharynx and avascular necrosis of bone; diabetic nephropathy and cardiomyopathy; and disorders of the female reproductive system such as endometriosis. The compounds can further be used for preventing the production of cyclooxygenase-2 and have analgesic properties. Therefore, Compounds of Formula I are useful for treatment of pain.

Other uses for Compounds of Formula I include treatment of HCV, severe asthma, psoriasis, chronic obstructive pulmonary disease (COPD), cancer, multiple myeloma, and other diseases that can be treated with an anti-TNF compound.

Besides being useful for human treatment, these compounds are also useful for veterinary treatment of companion animals, exotic animals and farm animals, including mammals, rodents, and the like. More preferred animals include horses, dogs, and cats.

The present compounds can also be used in co-therapies, partially or completely, in place of other conventional antiinflammatories, such as together with steroids, cyclooxygenase-2 inhibitors, NSAIDs, DMARDS, immunosuppressive agents, 5-lipoxygenase inhibitors, $LTB_4$ antagonists and $LTA_4$ hydrolase inhibitors.

As used herein, the term "TNF mediated disorder" refers to any and all disorders and disease states in which TNF plays a role, either by control of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disorder mediated by TNF.

As used herein, the term "p38 mediated disorder" refers to any and all disorders and disease states in which p38 plays a role, either by control of p38 itself, or by p38 causing another factor to be released, such as but not limited to IL-1, IL-6 or IL-8. A disease state in which, for instance, IL-1 is a major component, and whose production or action, is exacerbated or secreted in response to p38, would therefore be considered a disorder mediated by p38.

As TNF-β has close structural homology with TNF-α (also known as cachectin), and since each induces similar biologic responses and binds to the same cellular receptor, the synthesis of both TNF-α and TNF-β are inhibited by the compounds of the present invention and thus are herein referred to collectively as "TNF" unless specifically delineated otherwise.

EXAMPLES

The following preparations and examples are given to enable those skilled in the art to more clearly understand and to practice the present invention. They should not be considered as limiting the scope of the invention, but merely as being illustrative and representative thereof.

Unless otherwise stated, all temperatures including melting points (i.e., MP) are in degrees celsius (° C.). It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product. The following abbreviations may be used in the Examples.

Abbreviations

AcOH acetic acid
DCM dichloromethane
DMF N,N-dimethylformamide
DMAP 4-dimethylaminopyridine
EtOAc ethyl acetate
gc gas chromatography
HMPA hexamethylphosphoramide
hplc high performance liquid chromatography
mCPBA m-chloroperbenzoic acid
MeCN acetonitrile
MeOH methanol
TEA triethylamine
THF tetrahydrofuran
LDA lithium diisopropylamine
TLC thin layer chromatography
TMSBR trimethylsilyl bromide
uL microliter Example 1

This example illustrates a synthesis of succinic acid mono-[3-(2-chloro-phenyl)-6-(2,4-difluoro-phenoxy)-4-(2-(S)-hydroxy-propylamino)-pyrazolo[3,4-d]pyrimidin-1-ylmethyl] ester.

Step 1. Preparation of (2-chlorophenyl)-(4,6-dichloro-2-methylsulfanylpyrimidin-5-yl)-methanol

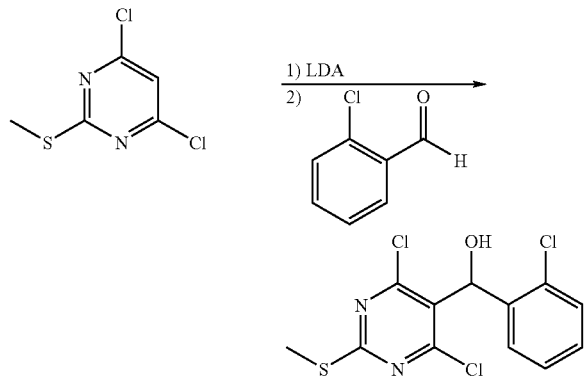

To a solution of 4,6-dichloro-2-(methylthio)pyrimidine (Aldrich) (5.0 g, 25.64 mmol) in dry THF (130 mL) at −78° C. under nitrogen was slowly added a solution of 2.0 M LDA (23.0 mL, 1.8 eq) in THF via a syringe. The resulting mixture was stirred at −78° C. for an additional 20 minutes, after which 2-chlorobenzaldehyde (Aldrich) (7.2 mL, 2 eq) was added dropwise via a syringe. The reaction mixture was stirred for an additional 30 minutes at −78° C. and then quenched with saturated ammonium chloride solution. Ethyl acetate was added, and the mixture was allowed to warm to room temperature. The aqueous layer was separated and extracted with ethyl acetate. The combined organic layers were washed with brine, dried over magnesium sulfate, filtered and concentrated to give the crude product (14.2 g) as an oil. Purification using Flash Column Chromatography on Silica Gel, eluting with 5% ethyl acetate in hexanes gave the title compound (8.60 g, (M+H)⁺=336, M.P.=109.5-112.5° C.) which crystallized upon standing to give a white solid.

Step 2. Preparation of (2-chlorophenyl)-(4,6-dichloro-2-methylsulfanylpyrimidin-5-yl)-methanone

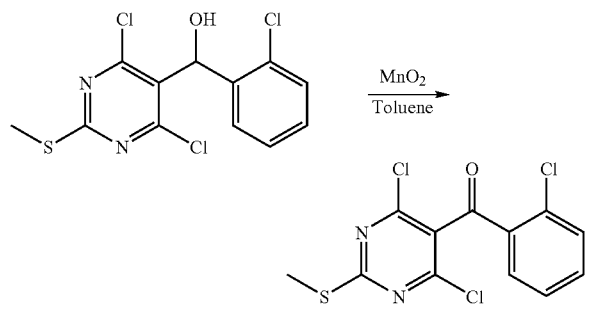

To a solution of (2-chlorophenyl)-(4,6-dichloro-2-methylsulfanylpyrimidin-5-yl)-methanol (8.6 g, 25.6 mmol) in toluene (300 mL) was added manganese (IV) oxide (Aldrich) (22.3 g, 10 eq), and the resulting mixture was heated to reflux with stirring for a total of 5 hours. The reaction was cooled to room temperature and then filtered through a 3.5 cm pad of Celite and the filtrate was concentrated to give 8.84 g of a crude product. Purification by Flash Column Chromatography on Silica Gel eluting with a gradient starting with pure hexanes and progressing to 2% ethyl acetate in hexanes and finally 5% ethyl acetate in hexanes gave the title compound as an off-white powder (1.388 g, (M+H)⁺=333).

Step 3. Preparation of 4-chloro-3-(2-chlorophenyl)-6-methylsulfanyl-1H-pyrazolo[3,4-d]pyrimidine

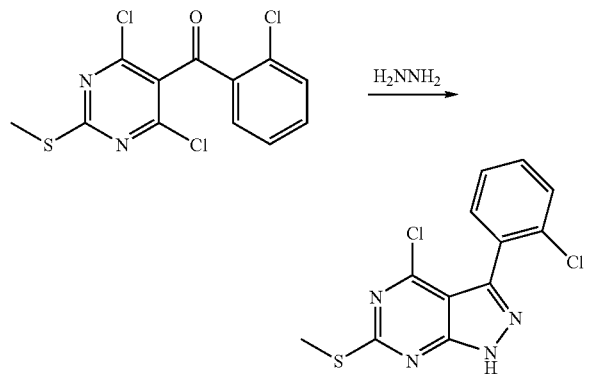

To a mixture of (2-chlorophenyl)-(4,6-dichloro-2-methylsulfanylpyrimidin-5-yl)-methanone (875 mg, 2.62 mmol) and N,N-diisopropyl ethyl amine (0.69 mL, 1.5 eq) in THF (20 mL) at 0° C. was added a solution of hydrazine (83 μL, 1 eq) in THF (20 mL) dropwise with stirring. After addition was complete, the reaction was gradually warmed to room temperature over 2 hours. Analysis by TLC indicated that there was still starting material remaining. Additional 3 mL of a solution of hydrazine (17 μL) in THF (10 mL) was added dropwise to the reaction mixture, and the reaction mixture was stirred at room temperature overnight. The reaction mixture was diluted with ethyl acetate (150 mL) and water (50 mL). The organic layer was separated, washed with water (4×50 mL) and brine (1×50 mL), dried over magnesium sulfate, filtered and concentrated to give the title compound as a yellowish powder (867 mg, (M+H)⁺=311).

Step 4. Preparation of (S)-1-[3-(2-chlorophenyl)-6-methylsulfanyl-1H-pyrazolo[3,4-d]pyrimidin-4-ylamino]-propan-2-ol

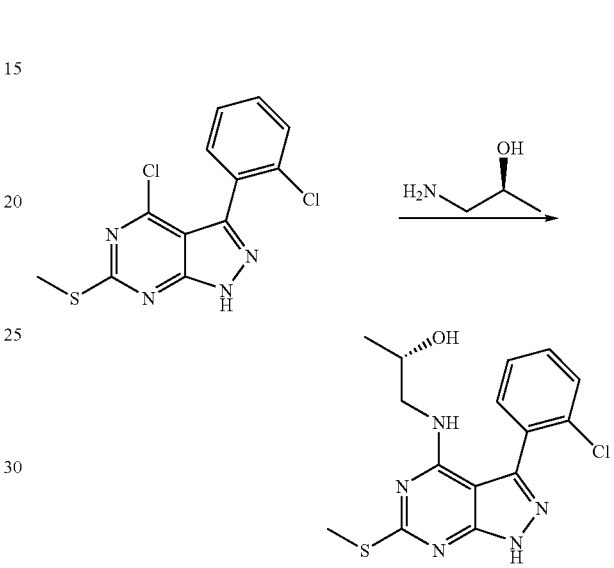

To a mixture of 4-chloro-3-(2-chloro-phenyl)-6-methylsulfanyl-1H-pyrazolo[3,4-d]pyrimidine (300 mg, 0.964 mmol) and N,N-diisopropylethyl amine (0.34 mL, 2 eq) in THF (5 mL) was added dropwise a solution of (S)-(+)-1-amino-2-propanaol (Aldrich) (0.217 g, 3 eq) in THF. The resulting mixture was stirred at room temperature overnight. The reaction was monitored by TLC analysis. The reaction mixture was diluted with ethyl acetate (150 mL) and water (70 mL). The organic layer was separated, washed with water (2×70 mL) and brine (1×70 mL), dried over magnesium sulfate, filtered and concentrated to give the title compound as an off-white solid (328 mg, (M+H)⁺=350).

Step 5. Preparation of (S)-1-[3-(2-chlorophenyl)-6-methanesulfonyl-1H-pyrazolo[3,4d]pyrimidin-4-ylamino]propan-2-ol

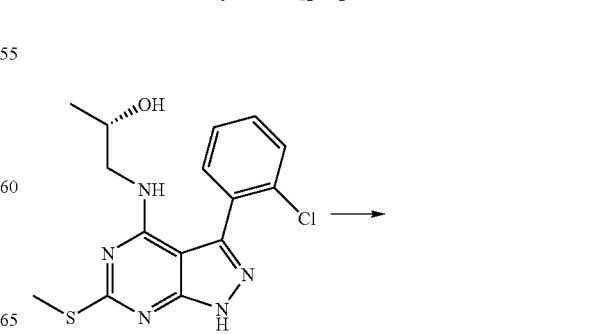

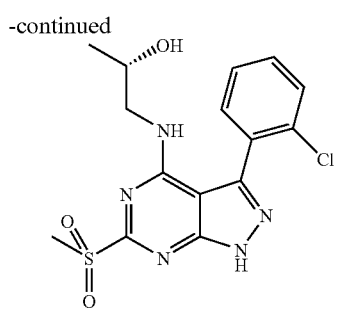

To a solution of (S)-1-[3-(2-chlorophenyl)-6-methylsulfanyl-1H-pyrazolo[3,4-d]pyrimidin-4-ylamino]propan-2-ol (320 mg, 0.915 mmol) in THF (15 mL) and methanol (5 mL) was added m-chloroperoxybenzoic acid (Aldrich) (431 mg, 2.1 eq) and the resulting mixture was stirred for 30 hours at room temperature. The reaction was monitored by TLC analysis. The reaction mixture was diluted with ethyl acetate (1170 mL) and saturated sodium bicarbonate (50 mL). The organic layer was separated, washed with saturated sodium bicarbonate (3×50 mL) and brine (1×50 mL), dried over magnesium sulfate, filtered and concentrated to give the title compound as an off-white powder (325 mg, $(M+H)^+=382$).

Step 6. Preparation of (S)-1-[3-(2-chlorophenyl)-6-(2,4-difluorophenoxy)-1H-pyrazolo[3,4-d]pyrimidin-4-ylamino]propan-2-ol

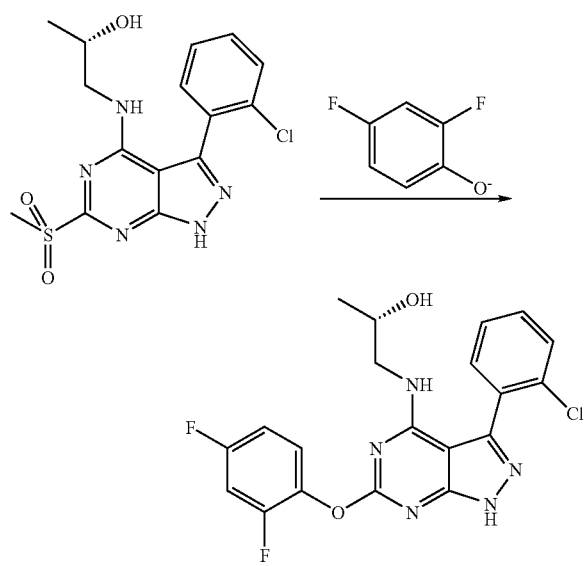

To a 0° C. solution of 2,4-difluorophenol (Aldrich) (0.15 mL, 4 eq) in DMSO (2 mL) in a Microwave Reactor Vessel was added a 1.0 M solution of potassium tert-butoxide in THF (1.61 mL, 4.1 eq). The resulting solution was warmed to room temperature and stirred for 10 minutes and then the reaction mixture was placed in the Microwave Reactor and heated at 150° C. for 1 hour. The reaction mixture was cooled and diluted with ethyl acetate (150 mL) and water (50 mL). The organic layer was separated, washed with water (2×50 mL) and brine (1×50 mL), dried over magnesium sulfate, filtered and concentrated to provide the crude compound (370 mg). Purification by Preparative Thin Layer Chromatography eluting with 5% methanol in dichloromethane gave the title compound as a white powder (109 mg, $(M+H)^+=432$, M.P.=254.6-258.2° C.).

Step 7. Preparation of 1-[3-(2-Chloro-phenyl)-6-(2,4-difluoro-phenoxy)-1-hydroxymethyl-1H-pyrazolo[3,4-d]pyrimidin-4-ylamino]-propan-2-ol

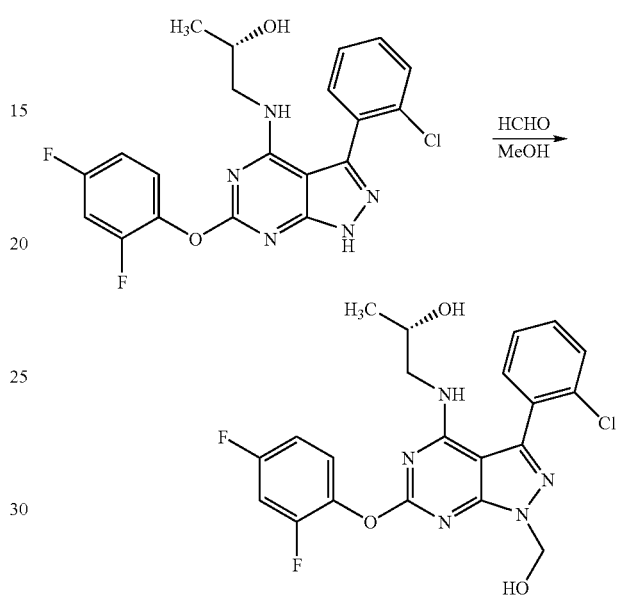

(S)-1-[3-(2-chlorophenyl)-6-(2,4-difluorophenoxy)-1H-pyrazolo[3,4-d]pyrimidin-4-ylamino]propan-2-ol (2.4 g, 5.5 mmol) was suspended in 50 mL MeOH and stirred. Formaldehyde (3.3 mL, excess) was added and the reaction mixture was stirred for 16 hours at room temperature. The reaction mixture was partitioned between water and ethyl acetate, and the organic layer was dried over $MgSO_4$, filtered and concentrated under reduced pressure to give 2.0 g of 1-[3-(2-Chloro-phenyl)-6-(2,4-difluoro-phenoxy)-1-hydroxymethyl-1H-pyrazolo[3,4-d]pyrimidin-4-ylamino]-propan-2-ol, MS (M+H)=462.

Step 8. Preparation of Succinic acid mono-[3-(2-chloro-phenyl)-6-(2,4-difluoro-phenoxy)-4-(2-(S)-hydroxy-propylamino)-pyrazolo[3,4-d]pyrimidin-1-ylmethyl]ester

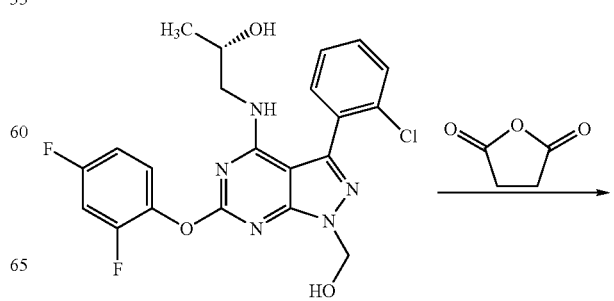

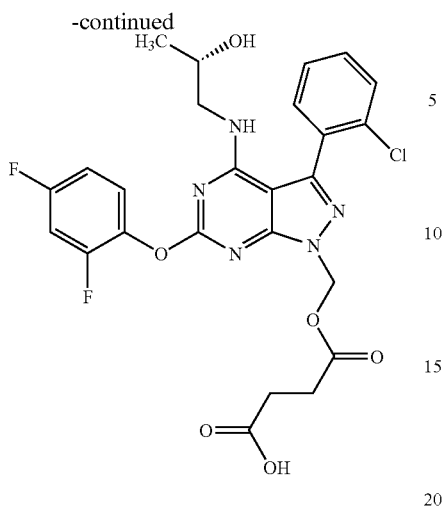

1-[3-(2-Chloro-phenyl)-6-(2,4-difluoro-phenoxy)-1-hydroxymethyl-1H-pyrazolo[3,4-d]pyrimidin-4-ylamino]-propan-2-ol (2.0 g, 4.3 mmol) was dissolved in 80 mL THF, and diisopropylamine (0.78 g, 5.6 mmol), dimethyamino pyridine (52 mg, 0.4 mmol) and succinic anhydride (703 mg, 7.0 mmol) were added while stirring at room temperature. The reaction mixture was stirred for 16 hours at room temperature, then partitioned between water and ethyl acetate, and the organic layer was dried over $MgSO_4$, filtered and concentrated under reduced pressure. The resulting residue was dissolved in EtOAc and purified by flash chromatography (silica gel, hexanes/EtOAc 1:1 to EtOAc/AcOH 100:1) to give 0.62 g of succinic acid mono-[3-(2-chloro-phenyl)-6-(2,4-difluoro-phenoxy)-4-(2-hydroxy-propylamino)-pyrazolo[3,4-d]pyrimidin-1-ylmethyl]ester, MS (M+H)=562

Additional compounds prepared according to the above example are shown in Table 1.

Example 2

This example illustrates a synthesis of (S)-phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester.

Step 1. Preparation of (S)-Phosphoric acid 2-[3-(2-chloro-phenyl)-6-(2,4-difluoro-phenoxy)-1H-pyrazolo[3,4-d]pyrimidin-4-ylamino]-1-methyl-ethyl ester dimethyl ester

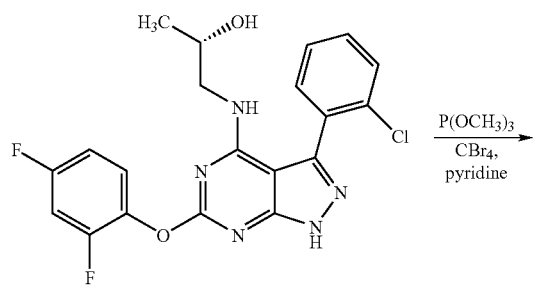

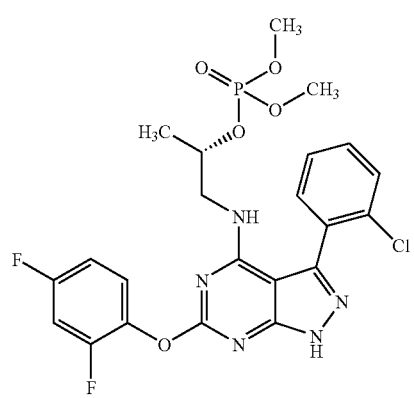

(S)-1-[3-(2-chlorophenyl)-6-(2,4-difluorophenoxy)-1H-pyrazolo[3,4-d]pyrimidin-4-ylamino]propan-2-ol (2.5 g, 5.79 mmol) was dissolved in 20 mL pyridine at room temperature, and the mixture was cooled to 0° C. with stirring. $P(OCH_3)_3$ (1.93 mL, excess) and $CBr_4$ (0.96 g) were added slowly, and the reaction mixture was allowed to warm up to room temperature over 20 minutes with stirring. The reaction mixture was poured into cold 1N HCl, and the resulting solution was extracted with EtOAc. The combined organic layers were washed with 1N HCl, followed by saturated aqueous $NaHCO_3$, then with saturated brine. The organic phase was dried over $MgSO_4$, filtered, and concentrated under reduced pressure. The residue was purified by flash chromatography (silica gel, 30%-60% EtOAc in methylene chloride) to give 3.132 g of phosphoric acid 2-[3-(2-chloro-phenyl)-6-(2,4-difluoro-phenoxy)-1H-pyrazolo[3,4-d]pyrimidin-4-ylamino]-1-methyl-ethyl ester dimethyl ester, MS (M+H)=540.

Step 2. Preparation of (S)-phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester

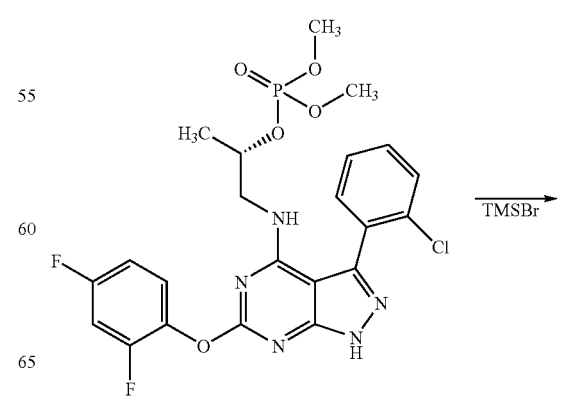

-continued

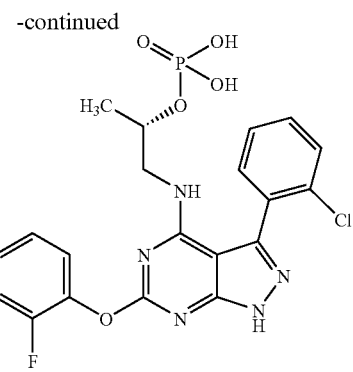

To (S)-phosphoric acid 2-[3-(2-chloro-phenyl)-6-(2,4-difluoro-phenoxy)-1H-pyrazolo[3,4-d]pyrimidin-4-ylamino]-1-methyl-ethyl ester dimethyl ester (3.1 g, 5.74 mmol) in 35 mL methylene chloride was added trimethylsilyl bromide (2.97 mL, excess) The reaction mixture was stirred for four hours at room temperature, and then solvent was removed under reduced pressure. Methanol (80 mL) was added, and the reaction mixture was stirred at room temperature. Solvent was again removed under reduced pressure, and the residue was added to 2N NaOH (100 mL) and EtOAc (mL). The mixture was stirred for 15 minutes, then the organic layer was separated, washed with saturated brine, dried over MgSO$_4$, filtered and concentrated under reduced pressure to give 2.243 g of (S)-phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester, MS (M+H)=512. This solid was converted to 2.182 g of the corresponding disodium salt by treatment with 15 Ml of 0.5M NaOCH$_3$ in MeOH; MP>300° C., MS (M+H)=512.

Additional compounds prepared according to the above example are shown in Table 1.

Example 3

2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester Step 1: Preparation of 4-Chloro-3-(2-chloro-phenyl)-6-methylsulfanyl-1-(2-trimethylsilanyl-ethoxymethyl)-1H-pyrazolo[3,4-d]pyrimidine

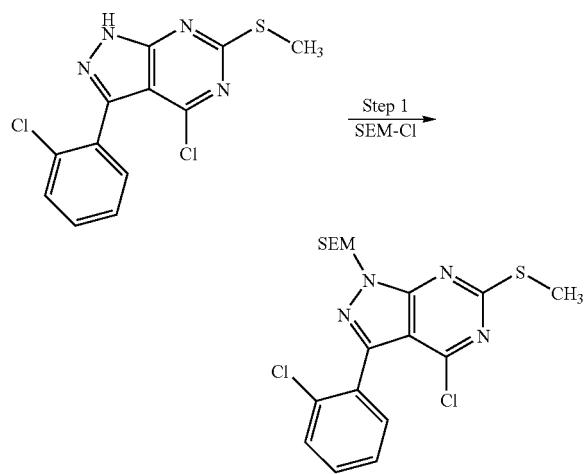

To a solution of 4-chloro-3-(2-chloro-phenyl)-6-methylsulfanyl-1H-pyrazolo[3,4-d]pyrimidine (2.30 g, 7.39 mmol) and 2-(trimethylsilyl)-ethoxymethylene chloride (1.96 mL, 11.086 mmol) in dry DMF (40 mL) at 0° C. under nitrogen was added sodium hydride (0.354 g of 60% solids in mineral oil, 14.78 mmol). The reaction mixture was stirred for two hours and allowed to warm to room temperature during this time. The reaction mixture was partitioned between water and ethyl acetate, and the organic layer was separate, washed with brine, dried over MgSO$_4$, filtered and concentrated under reduced pressure. The residue was chromatographed on silica (01% to 20% EtOAc in hexanes) to give 2.30 g of 4-chloro-3-(2-chloro-phenyl)-6-methylsulfanyl-1-(2-trimethylsilanyl-ethoxymethyl)-1H-pyrazolo[3,4-d]pyrimidine Step 2. Preparation of (S)-1-[3-(2-Chloro-phenyl)-6-methylsulfanyl-1-(3-trimethylsilanyl-propoxy)-1H-pyrazolo[3,4-d]pyrimidin-4-ylamino]-propan-2-ol

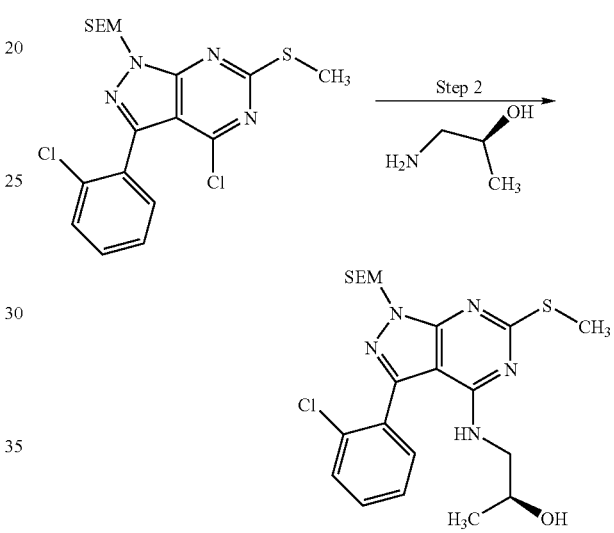

To a solution of 4-chloro-3-(2-chloro-phenyl)-6-methylsulfanyl-1-(2-trimethylsilanyl-ethoxymethyl)-1H-pyrazolo[3,4-d]pyrimidine (2.30 g, 5.21 mmol) in 45 mL dry THF was added (S)-1-amino-propan-2-ol (1.565 g, 20.84 mmol). The reaction mixture was stirred for 18 hours, and then partitioned between water and ethyl acetate. The organic layer was separate, washed with brine, dried over MgSO$_4$, filtered and concentrated under reduced pressure to give 2.42 g of (S)-1-[3-(2-chloro-phenyl)-6-methylsulfanyl-1-(3-trimethylsilanyl-propoxy)-1H-pyrazolo[3,4-d]pyrimidin-4-ylamino]-propan-2-ol.

Step 3. Preparation of (S)-1-[3-(2-Chloro-phenyl)-1-(3-dimethylsilanyl-propoxy)-6-methanesulfonyl-1H-pyrazolo[3,4-d]pyrimidin-4-ylamino]-propan-2-ol

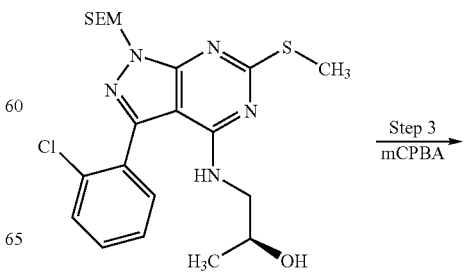

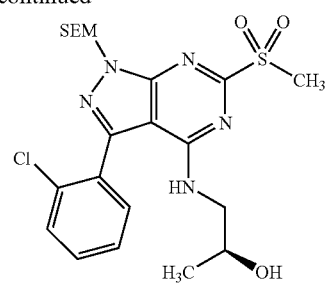

(S)-1-[3-(2-Chloro-phenyl)-6-methylsulfanyl-1-(3-trimethylsilanyl-propoxy)-1H-pyrazolo[3,4-d]pyrimidin-4-ylamino]-propan-2-ol (2.41 g, 5.02 mmol) was dissolved in 50 mL THF, and meta-chloroperbenzoic acid (2.36 g of 77% solids, 10.54 mmol) was added. The reaction mixture was stirred at room temperature for 18 hours and then partitioned between water and ethyl acetate. The organic layer was separate, washed with brine and saturated aqueous sodium bicarbonate, dried over $MgSO_4$, filtered and concentrated under reduced pressure to give 2.10 g of (S)-1-[3-(2-chloro-phenyl)-1-(3-dimethylsilanyl-propoxy)-6-methanesulfonyl-1H-pyrazolo[3,4-d]pyrimidin-4-ylamino]-propan-2-ol.

Step 4: Preparation of (S)-1-[3-(2-Chloro-phenyl)-6-(2,4-difluoro-phenoxy)-1-(3-trimethylsilanyl-propoxy)-1H-pyrazolo[3,4-d]pyrimidin-4-ylamino]-propan-2-ol

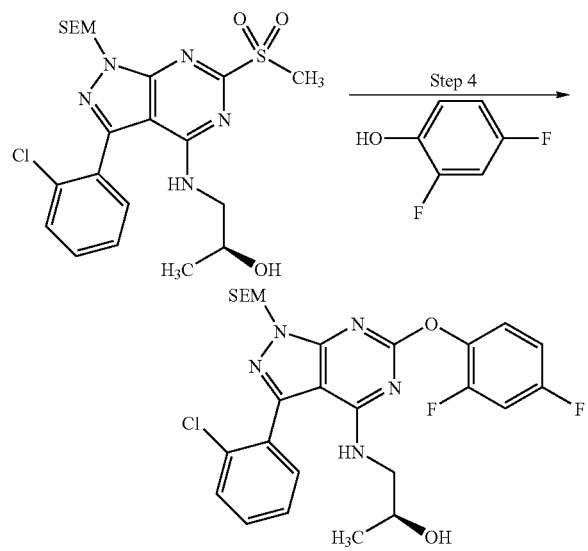

(S)-1-[3-(2-Chloro-phenyl)-1-(3-dimethylsilanyl-propoxy)-6-methanesulfonyl-1H-pyrazolo[3,4-d]pyrimidin-4-ylamino]-propan-2-ol (2.09 g, 4.00 mmol) was converted to 1.59 g of (S)-1-[3-(2-chloro-phenyl)-6-(2,4-difluoro-phenoxy)-1-(3-trimethylsilanyl-propoxy)-1H-pyrazolo[3,4-d]pyrimidin-4-ylamino]-propan-2-ol using the procedure of step 6 of Example 1.

Step 5: Preparation of (S)-2-tert-Butoxycarbonylamino-3-methyl-butyric acid (S)-2-[3-(2-chlorophenyl)-6-(2,4-difluoro-phenoxy)-1-methyl-1H-pyrazolo[3,4-d]pyrimidin-4-ylamino]-1-methyl-ethyl ester

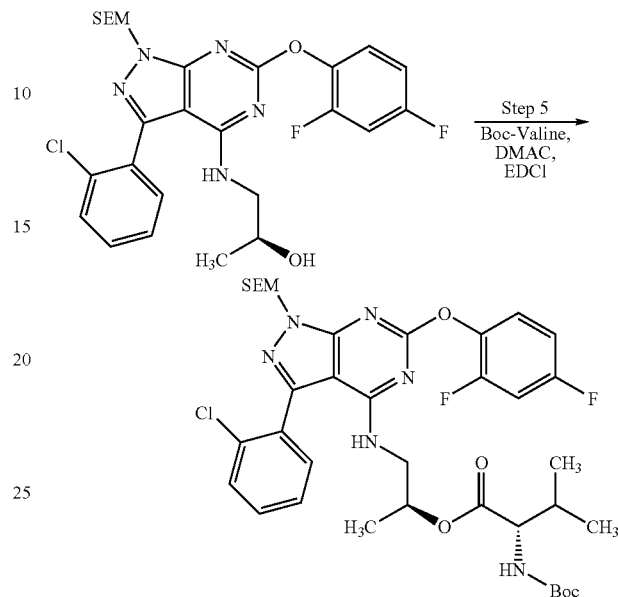

A solution of (S)-1-[3-(2-Chloro-phenyl)-6-(2,4-difluoro-phenoxy)-1-(3-trimethylsilanyl-propoxy)-1H-pyrazolo[3,4-d]pyrimidin-4-ylamino]-propan-2-ol (50 mg, 0.2846 mmol), Boc-(L)-Valine (68 mg, 0.313 mmol), 4-dimethylaminopyridine (7 mg, 0.057 mmol) and 1-(3-dimethylaminopropyl)-3-ethylcarodiimide (60 mg, 0.313 mmol) in 4 mL DMF was stirred at room temperature for three days, then heated to 120° C. for four hours. The reaction mixture was cooled and partitioned between water and ethyl acetate. The organic layer was separate, washed with 0.5N aqueous HCl, saturated aqueous sodium bicarbonate and brine, dried over $MgSO_4$, filtered and concentrated under reduced pressure. The residue was chromatographed on silica (0% to 50% EtOAc in hexanes) to give 50 mg of (S)-2-tert-butoxycarbonylamino-3-methyl-butyric acid (S)-2-[3-(2-chloro-phenyl)-6-(2,4-difluoro-phenoxy)-1-methyl1H-pyrazolo[3,4-d]pyrimidin-4-ylamino]-1-methyl-ethyl ester Step 6: Preparation of 2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester

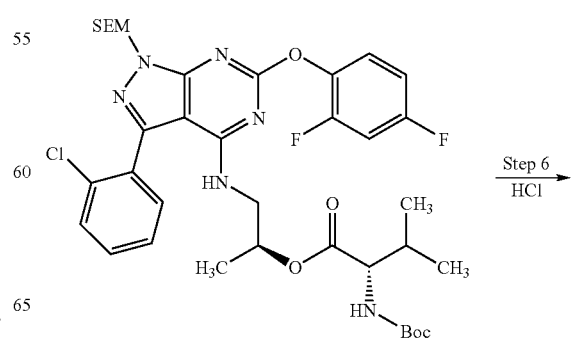

-continued

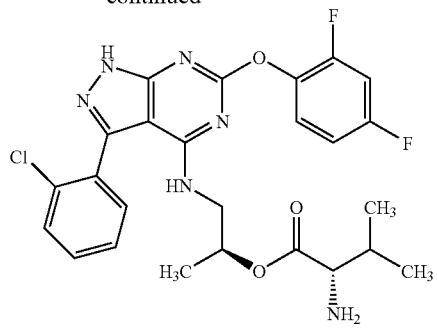

A mixture of (S)-3-methyl-2-methylamino-butyric acid (S)-2-[3-(2-chloro-phenyl)-6-(2,4-difluoro-phenoxy)-1-(3-trimethylsilanyl-propoxy)-1H-pyrazolo[3,4-d]pyrimidin-4-ylamino]-1-methyl-ethyl ester (15 mg, 0.0197 mmol), HCl (1 mL of 5N aqueous solution) and dioxane (1 mL) was heated to 80° C. for 30 minutes and then cooled to room temperature. The reaction mixture was made mildly basic by addition of saturated aqueous sodium bicarbonate solution, and the resulting precipitate was filtered, washed with water and dried under vacuum to afford 7 mg of 2-amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester.

Example 4

2-Amino-3-methyl-butyric acid 6-(2,4-difluoro-phenoxy)-3-(2,5-difluoro-phenyl)-4-(2-methanesulfonyl-ethylamino)-pyrazolo[3,4-d]pyrimidin-1-ylmethyl ester Step 1: 2-tert-Butoxycarbonylamino-3-methyl-butyric acid 6-(2,4-difluoro-phenoxy)-3-(2,5-difluoro-phenyl)-4-(2-methanesulfonyl-ethylamino)-pyrazolo[3,4-d]pyrimidin-1-ylmethyl ester

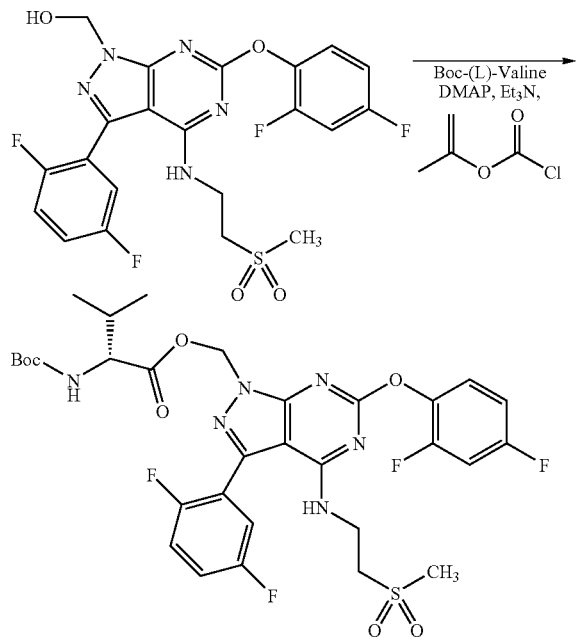

[6-(2,4-Difluoro-phenoxy)-3-(2,5-difluoro-phenyl)-4-(2-methanesulfonyl-ethylamino)-pyrazolo[3,4-d]pyrimidin-1-yl]-methanol (170 mg, 0.33 mmol) was dissolved in methylene chloride, and Boc-(L)-Valine (216 mg, 0.99 mmol), dimethylamino pyridine (81 mg, 0.66 mmol), and triethylamine (0.23 mL, 1.6 mmol) were added. The reaction mixture was cooled to 0° C. and stirred under nitrogen, and isopropenyl chloroformate (54 uL, 0.49 mmol) was added. The reaction mixture was stirred for 10 minutes and then partitioned between water and methylene chloride. The organic layer was washed with brine, dried (MgSO$_4$), filtered and concentrated under reduced pressure. The residue was purified by flash chromatography through silica (1:1 hexanes/EtOAc) to give 120 mg of 2-tert-butoxycarbonylamino-3-methyl-butyric acid 6-(2,4-difluoro-phenoxy)-3-(2,5-difluoro-phenyl)-4-(2-methanesulfonyl-ethylamino)-pyrazolo[3,4-d]pyrimidin-1-ylmethyl ester as an oil.

Step 2: 2-Amino-3-methyl-butyric acid 6-(2,4-difluoro-phenoxy)-3-(2,5-difluoro-phenyl)-4-(2-methanesulfonyl-ethylamino)-pyrazolo[3,4-d]pyrimidin-1-ylmethyl ester

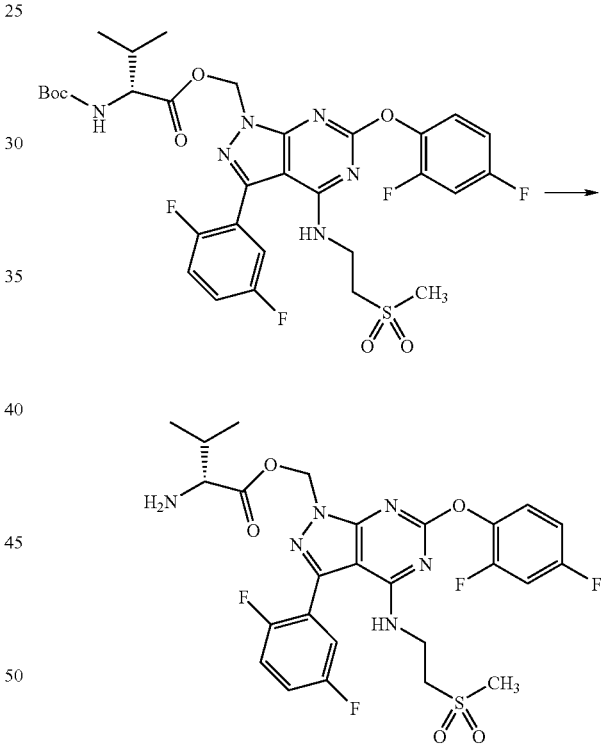

2-tert-Butoxycarbonylamino-3-methyl-butyric acid 6-(2,4-difluoro-phenoxy)-3-(2,5-difluoro-phenyl)-4-(2-methanesulfonyl-ethylamino)-pyrazolo[3,4-d]pyrimidin-1-ylmethyl ester (110 mg, 0.15 mmol) was dissolved in Et$_2$O and treated with 4 mL of HCl.Et$_2$O. The reaction mixture was stirred for three hours at room temperature, then concentrated under reduced pressure to afford 100 mg of 2-amino-3-methyl-butyric acid 6-(2,4-difluoro-phenoxy)-3-(2,5-difluoro-phenyl)-4-(2-methanesulfonyl-ethylamino)-indazol-1-ylmethyl ester, MS (M+H)=611.

Example 5

Phosphoric acid mono-[6-(2,4-difluoro-phenoxy)-3-(2,5-difluoro-phenyl)-4-(2-methanesulfonyl-ethylamino)-pyrazolo[3,4-d]pyrimidin-1-ylmethyl]ester

Step 1: Phosphoric acid di-tert-butyl ester 6-(2,4-difluoro-phenoxy)-3-(2,5-difluoro-phenyl)-4-(2-methanesulfonyl-ethylamino)-pyrazolo[3,4-d]pyrimidin-1-ylmethyl ester

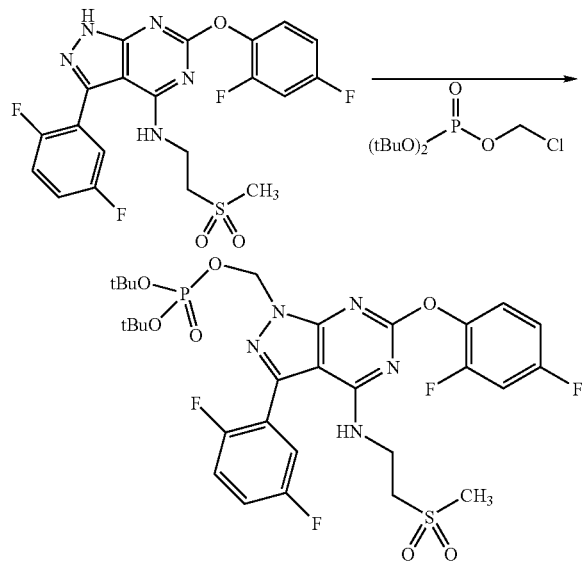

Bis(tert-butoxy) chloromethyl phosphate (410 mg, 1.5 mmol) was dissolved in acetonitrile, and [6-(2,4-difluoro-phenoxy)-3-(2,5-difluoro-phenyl)-1H-pyrazolo[3,4-d]pyrimidin-4-yl]-(2-methanesulfonyl-ethyl)-amine (180 mg, 0.37 mmol) and cesium carbonate (300 mg, 0.92 mmol) were added. The reaction mixture was heated to 80° C. with stirring for two hours, then cooled to room temperature, filtered to remove insolubles, and the filtrate was concentrated under reduced pressure. The residue was purified by flash chromatography (50% to 100% hexanes in EtOAc) through silica to give 190 mg of phosphoric acid di-tert-butyl ester 6-(2,4-difluoro-phenoxy)-3-(2,5-difluoro-phenyl)-4-(2-methanesulfonyl-ethylamino)-pyrazolo[3,4-d]pyrimidin-1-ylmethyl ester

Step 2: Phosphoric acid mono-[6-(2,4-difluoro-phenoxy)-3-(2,5-difluoro-phenyl)-4-(2-methanesulfonyl-ethylamino)-pyrazolo[3,4-d]pyrimidin-1-ylmethyl]ester

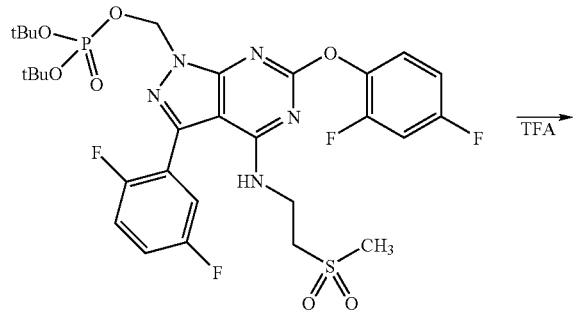

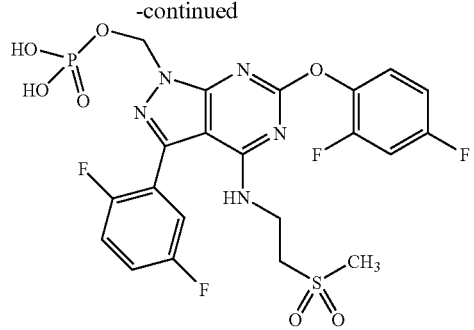

Phosphoric acid di-tert-butyl ester 6-(2,4-difluoro-phenoxy)-3-(2,5-difluoro-phenyl)-4-(2-methanesulfonyl-ethylamino)-indazol-1-ylmethyl ester (180 mg, 0.25 mmol) was dissolved in methylene chloride and treated with trifluoroacetic acid (29 uL, 0.51 mmol). The reaction mixture was stirred at room temperature for five hours, then concentrated under reduced pressure. The residue was triturated with methylene chloride and concentrated under reduced pressure to give 40 mg of phosphoric acid mono-[6-(2,4-difluoro-phenoxy)-3-(2,5-difluoro-phenyl)-4-(2-methanesulfonyl-ethylamino)-pyrazolo[3,4-d]pyrimidin-1-ylmethyl]ester.

Example 6

Determination of Pharmacokinetic Parameters of 1-[3-(2-chloro-phenyl)-6-(2,4-difluoro-phenoxy)-1H-pyrazolo[3,4-d]pyrimidin-4-ylamino]-propan-2-ol and its prodrug phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester after the Administration of the prodrug phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester Male Crl:WI(GLx/BRL/Han)IGS BR (Hanover-Wistar) rats weighing 240-260 g were cannulated. Groups of three rats were used for each dose level of an experimental compound. One additional non-cannulated animal was included as vehicle control. Animals were allowed normal access to food and water throughout the experiment. The test substance phosphoric acid mono-{2-[3-(2-chloro-phenyl)-6-(2,4-difluoro-phenoxy)-1H-pyrazolo[3,4-d]pyrimidin-4-ylamino]-1-methyl-ethyl}ester was formulated as an aqueous suspension and a dose of 3 or 30 mg/kg (in 1-[3-(2-chloro-phenyl)-6-(2,4-difluoro-phenoxy)-1H-pyrazolo[3,4-d]pyrimidin-4-ylamino]-propan-2-ol equivalent) was administered orally through gavage. A blood sample (0.3 mL) was collected from the each treated rat at 0 (predose), 0.083, 0.25, 1, 2, 4, 6, and 8 hr after dose via the jugular cannula. At 24 hr after dosing, blood was collected from each treated rat via cardiac puncture. Blood was also collected from the untreated animal at 24 hr via cardiac puncture. Lithium heparin was added to the samples which were stored on ice during sampling procedure. The samples were spun in a refrigerated centrifuge at 4° C. as soon as possible and the plasma samples were stored −20° C. immediately after centrifugation and until analysis. The concentration of test compound was determined by HPLC-MS/MS. Using the above procedure, $C_{max}$ of 1.33 and 9.80 μg/mL (for 3 mg/kg and 30 mg/kg, respectively) and AUC of 12.6 and 124 μg*h/mL (for 3 mg/kg and 30 mg/kg, respectively) were measured for the compound 1-[3-(2-chloro-phenyl)-6-(2,4-difluoro-phenoxy)-1H-pyrazolo[3,4-d]pyrimidin-4-ylamino]-propan-2-ol. The prodrug phosphoric acid mono- {2-[3-(2-chloro-phenyl)-6-(2,4-difluoro-phenoxy)-1H-pyrazolo[3,4-d]pyrimidin-4-ylamino]-1-methyl-ethyl}ester was not detected in the rat plasma (at quantification limit of 0.0005 µg/mL) with the 3-mg/kg dose. A $C_{max}$ of 0.214 µg/mL and AUC of 0.188 µg*h/mL were measured for the prodrug with the 30-mg/kg dose.

Example 7

Determination of Pharmacokinetic Parameters of 1-[3-(2-Chloro-phenyl)-6-(2,4-difluoro-phenoxy)-1H-pyrazolo[3,4-d]pyrimidin-4-ylamino]-2-methyl-propan-2-ol and its prodrug succinic acid mono-[3-(2-chloro-phenyl)-6-(2,4-difluoro-phenoxy)-4-(2-hydroxy-2-methyl-propylamino)-pyrazolo[3,4-d]pyrimidin-1-ylmethyl]ester after the Administration of the prodrug succinic acid mono-[3-(2-chloro-phenyl)-6-(2,4-difluoro-phenoxy)-4-(2-hydroxy-2-methyl-propylamino)-pyrazolo [3,4-d]pyrimidin-1-ylmethyl]ester Male Crl:WI(GLx/BRL/Han)IGS BR (Hanover-Wistar) rats weighing 240-260 g were cannulated. Groups of three rats were used for each dose level of an experimental compound. The test substance succinic acid mono-[3-(2-chloro-phenyl)-6-(2,4-difluoro-phenoxy)-4-(2-hydroxy-2-methyl-propylamino)-pyrazolo[3,4-d]pyrimidin-1-ylmethyl]ester was formulated as an aqueous suspension, and a dose of 3 or 10 mg/kg (in 1-[3-(2-Chloro-phenyl)-6-(2,4-difluoro-phenoxy)-1H-pyrazolo[3,4-d]pyrimidin-4-ylamino]-2-methyl-propan-2-ol equivalent) was administered orally through gavage. A blood sample (0.3 mL) was collected from the each treated rat at 0 (predose), 0.083, 0.25, 1, 2, 4, 6, and 8 h after dose via the jugular cannula. At 24 h after dosing, blood was collected from each treated rat via cardiac puncture. Lithium heparin was added to the samples which were stored on ice during sampling procedure. The samples were spun in a refrigerated centrifuge at 4° C. as soon as possible and the plasma samples were stored –20° C. immediately after centrifugation and until analysis. The concentration of test compound was determined by HPLC-MS/MS. Using the above procedure, $C_{max}$ of 1.34 and 7.05 µg/mL and AUC of 9.27 and 47.4 µg*h/mL were measured for the compound 1-[3-(2-Chloro-phenyl)-6-(2,4-difluoro-phenoxy)-1H-pyrazolo[3,4-d]pyrimidin-4-ylamino]-2-methyl-propan-2-ol for 3-mg/kg and 10-mg/kg doses, respectively. For the prodrug succinic acid mono-[3-(2-chloro-phenyl)-6-(2,4-difluoro-phenoxy)-4-(2-hydroxy-2-methyl-propylamino)-pyrazolo[3,4-d]pyrimidin-1-ylmethyl]ester $C_{max}$ of 1.83 and 9.25 µg/mL, and AUC of 6.11 and 20.9 µg*h/mL were measured, for 3-mg/kg and 10-mg/kg doses, respectively.

Example 8

This example illustrates a p38 (MAP) kinase in vitro assay useful for evaluating the compounds of the invention.

The p38 MAP kinase inhibitory activity of compounds of this invention in vitro was determined by measuring the transfer of the γ-phosphate from γ-$^{33}$P-ATP by p-38 kinase to Myelin Basic Protein (MBP), using a minor modification of the method described in Ahn, et al., *J. Biol. Chem.* 266:4220-4227 (1991).

The phosphorylated form of the recombinant p38 MAP kinase was co-expressed with SEK-1 and MEKK in *E. Coli* (see, Khokhlatchev, et al., *J. Biol. Chem.* 272:11057-11062 (1997)) and then purified by affinity chromatography using a Nickel column.

The phosphorylated p38 MAP kinase was diluted in kinase buffer (20 mM 3-(N-morpholino)propanesulfonic acid, pH 7.2, 25 mM β-glycerol phosphate, 5 mM ethylene glycol-bis (beta-aminoethyl ether)-N,N,N',N'-tetraacetic acid, 1 mM sodium ortho-vanadate, 1 mM dithiothreitol, 40 mM magnesium chloride). Test compound dissolved in DMSO or only DMSO (control) was added and the samples were incubated for 10 min at 30° C. The kinase reaction was initiated by the addition of a substrate cocktail containing MBP and γ-$^{33}$P-ATP. After incubating for an additional 20 min at 30° C., the reaction was terminated by adding 0.75% phosphoric acid. The phosphorylated MBP was then separated from the residual γ-$^{33}$P-ATP using a phosphocellulose membrane (Millipore, Bedfrod, Mass.) and quantitated using a scintillation counter (Packard, Meriden, Conn.).

Using the above procedure, the compounds of the invention were found to be inhibitors of p38 MAP kinase. For example, parent compound 3-[3-(2-Chloro-phenyl)-6-(2,4-difluoro-phenoxy)-1H-pyrazolo[3,4-d]pyrimidin-4-ylamino]-propane-1,2-diol exhibited a p38 $IC_{50}$ (uM) of 0.004.

Example 9

In Vitro Assay to Evaluate the Inhibition of LPS-Induced TNF-α Production in THP1 Cells This example illustrates an in vitro assay to evaluate the inhibition of LPS-induced TNF-α production in THP1 cells.

The ability of the compounds of this invention to inhibit the TNF-α release is determined using a minor modification of the methods described in Blifeld, et al. *Transplantation*, 51:498-503 (1991).

(a) Induction of TNF Biosynthesis:

THP-1 cells are suspended in culture medium [RPMI (Gibco-BRL, Gailthersburg, Md.) containing 15% fetal bovine serum, 0.02 mM 2-mercaptoethanol], at a concentration of 2.5×10$^6$ cells/mL and then plated in 96 well plate (0.2 mL aliquots in each well). Test compounds are dissolved in DMSO and then diluted with the culture medium such that the final DMSO concentration is 5%. Twenty five µL aliquots of test solution or only medium with DMSO (control) are added to each well. The cells are incubated for 30 min., at 37° C. LPS (Sigma, St. Louis, Mo.) is added to the wells at a final concentration of 0.5 µg/ml, and cells were incubated for an additional 2 h. At the end of the incubation period, culture supernatants are collected and the amount of TNF-α present is determined using an ELISA assay as described below.

(b) ELISA Assay:

The amount of human TNF-α present is determined by a specific trapping ELISA assay using two anti-TNF-α antibodies (2TNF-H12 and 2TNF-H34) described in Reimund, J. M., et al. *GUT.* Vol. 39(5), 684-689 (1996).

Polystyrene 96-well plates are coated with 50 µl per well of antibody 2TNF-H12 in PBS (10 µg/mL) and incubated in a humidified chamber at 4° C. overnight. The plates are washed with PBS and then blocked with 5% nonfat-dry milk in PBS for 1 hour at room temperature and washed with 0.1% BSA (bovine serum albumin) in PBS.

TNF standards are prepared from a stock solution of human recombinant TNF-α (R&D Systems, Minneapolis, Minn.). The concentration of the standards in the assay began at 10 ng/mL followed by 6 half log serial dilutions.

Twenty five µL aliquots of the above culture supernatants or TNF standards or only medium (control) are mixed with 25 µL aliquots of biotinylated monoclonal antibody 2TNF-H34 (2 µg/mL in PBS containing 0.1% BSA) and then added to each well. The samples are incubated for 2 hr at room temperature with gentle shaking and then washed 3 times with 0.1% BSA in PBS. 50 µl of peroxidase-streptavidin (Zymed, S. San Francisco, Calif.) solution containing 0.416 µg/mL of peroxidase-streptavidin and 0.1% BSA in PBS was added to each well. The samples are incubated for an additional 1 hr at room temperature and then washed 4 times with 0.1% BSA in PBS. Fifty μL of O-phenylenediamine solution (1 μg/mL O-phenylene-diamine and 0.03% hydrogen peroxide in 0.2M citrate buffer pH 4.5) is added to each well and the samples are incubated in the dark for 30 min., at room temperature. Optical density of the sample and the reference are read at 450 nm and 650 nm, respectively. TNF-α levels are determined from a graph relating the optical density at 450 nm to the concentration used.

Example 10

In Vitro Assay to Evaluate the Inhibition of LPS-Induced TNF-α Production in THP1 Cells This example illustrates an in vivo assay to evaluate the inhibition of LPS-induced TNF-α production in mice (or rats).

The ability of the compounds of this invention to inhibit the TNF-α release, in vivo, is determined using a minor modification of the methods described in described in Zanetti, et. al., *J. Immunol.*, 148:1890 (1992) and Sekut, et. al., *J. Lab. Clin. Med.*, 124:813 (1994).

Female BALB/c mice weighing 18-21 grams (Charles River, Hollister, Calif.) are acclimated for one week. Groups containing 8 mice each are dosed orally either with the test compounds suspended or dissolved in an aqueous vehicle containing 0.9% sodium chloride, 0.5% sodium carboxymethyl-cellulose, 0.4% polysorbate 80, 0.9% benzyl alcohol (CMC vehicle) or only vehicle (control group). After 30 min., the mice are injected intraperitoneally with 20 μg of LPS (Sigma, St. Louis, Mo.). After 1.5 h, the mice are sacrificed by $CO_2$ inhalation and blood is harvested by cardiocentesis. Blood is clarified by centrifugation at 15,600×g for 5 min., and sera are transferred to clean tubes and frozen at −20° C. until analyzed for TNF-α by ELISA assay (Biosource International, Camarillo, Calif.) following the manufacturer's protocol.

Example 11

Adjuvant-Induced Arthritis in Rats

AIA-induced arthritis is evaluated using the procedure of Badger et al., *Arthritis & Rheumatism,* 43(1) pp 175-183 (2000) AIA is induced by a single injection of 0.75 mg of parrafin-suspended *Mycobacterium Butycricum*) into male Lewis rats. Hindpaw volume is measured by water displacement on days 15, 20 and 30. A set of control animals is dosed with tragacanth. Test compounds in 0.5% tragacanth are administered orally at 3, 10, 30 and 60 mg/kg/day dosages. Indomethacin is used as a positive control. Percentage inhibition of hindpaw edema is calculated by 1−[*AIA*(treated)/*AIA* (control)]×100 where AIA (treated) and AIA (control) represent the mean paw volume.

Example 12

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of formula Ia:

Ia or a pharmaceutically acceptable salt thereof, wherein:
$R^1$ is optionally substituted phenyl;
$R^2$ is optionally substituted phenyl
$R^4$ is hydroxyalkyl, alkoxyalkyl or alkylsulfonylalkyl $R^5$ is hydrogen, —C(=O)—$R^c$, —(O=)P(O$R^d$)$_2$, —S(=O)$_2$O$R^d$, or a mono-, di- or tri-peptide;
wherein
$R^c$ is —(CH$_2$)$_p$—C(=O)—$R^e$;
wherein
$R^e$ is hydrogen, hydroxy, alkoxy or amine;
p is 2 or 3;
$R^d$ is hydrogen, alkyl, an alkali metal ion or an alkaline earth metal ion;
X and Y are nitrogen;
D is —(CR$^7$R$^8$)$_n$—;
wherein
n is from 1 to 3;
$R^7$ and $R^8$ each independently is hydrogen or alkyl;
W is a bond or N$R^i$;
$R^i$ is hydrogen;
A is O; and
k is 0.

2. The compound of claim 1, wherein n is 1.
3. The compound of claim 2, wherein $R^7$ and $R^8$ are hydrogen.
4. The compound of claim 3, wherein $R^5$ is hydrogen.
5. The compound of claim 3, wherein $R^5$ is —C(=O)—$R^c$.
6. The compound of claim 5, wherein p is 2.
7. The compound of claim 1, wherein $R^5$ is —(O=)P(O$R^d$)$_2$— and $R^d$ is hydrogen.
8. The compound of claim 1, wherein said compound is of the formula IVa IVa wherein
u is 1 or 2;
v is 1 or 2;
each $R^9$ is independently halo;
each $R^{10}$ is independently halo or alkylsulfonyl and
W, D, $R^4$ and $R^5$ are as recited in claim 1.

9. A composition comprising:
(a) a pharmaceutically acceptable excipient; and
(b) a compound of claim 1.

10. A compound selected from the group consisting of:
Succinic acid mono-[3-(2-chloro-phenyl)-6-(2,4-difluoro-phenoxy)-4-(2-hydroxyl-propylamino)-pyrazolo[3,4-d]pyrimidin-1-ylmethyl] ester;
Succinic acid mono-[3-(2-chloro-phenyl)-6-(2,4-difluoro-phenoxy)-4-(2-hydroxyl-2-methyl-propylamino)-pyrazolo[3,4-d]pyrimidin-1-ylmethyl] ester;
Succinic acid mono-[3-(2-chloro-phenyl)-6-(2,4-difluoro-phenoxy)-4-(2-methanesulfonyl-ethylamino)-pyrazolo[3,4-d]pyrimidin-1-ylmethyl] ester;
[3-(2-Chloro-phenyl)-6-(2,4-difluoro-phenoxy)-4-(2-methanesulfonyl-ethylamino)-pyrazolo[3,4-d]pyrimidin-1-yl]-methanol;
Phosphoric acid mono-[3-(2-chloro-phenyl)-6-(2,4-difluoro-phenoxy)-4-(2-methanesulfonyl-ethylamino)-pyrazolo[3,4-d]pyrimidin-1-ylmethyl] ester;
Succinic acid mono-[3-(2-chloro-phenyl)-6-(2,4-difluoro-phenoxy)-pyrazolo[3,4-d]pyrimidin-1-ylmethyl] ester;
[3-(2-Chloro-phenyl)-6-(2,4-difluoro-phenoxy)-pyrazolo[3,4-d]pyrimidin-1-yl]-methanol;

1-[3-(2-Chloro-phenyl)-6-(2,4-difluoro-phenoxy)-1-hydroxymethyl-1H-pyrazolo[3,4-d]pyrimidin-4-ylamino]-propan-2-ol;

1-[3-(2-Chloro-phenyl)-6-(2,4-difluoro-phenoxy)-1-hydroxymethyl-1H-pyrazolo[3,4-d]pyrimidin-4-ylarmino]-2-methyl-propan-2-ol;

Phosphoric acid mono-[3-(2-chloro-phenyl)-6-(2,4-difluoro-phenoxy)-4-(2-hydroxy-propylamino)-pyrazolo[3,4-d]pyrimidin-1-ylmethyl] ester;

2-Amino-3-methyl-butyric acid 3-(2-chloro-phenyl)-6-(2,4-difluoro-phenoxy)-4-(2-methanesulfonyl-ethylamino)-pyrazolo[3,4-d]pyrimidin-1-ylmethyl ester;

Phosphoric acid mono-{2-[3-(2-chloro-phenyl)-6-(2,4-difluoro-phenoxy)-1H-pyrazolo[3,4-d]pyrimidin-4-ylamino]-1-methyl-ethyl} ester;

Phosphoric acid mono-{2-[3-(2-chloro-phenyl)-6-(2,4-difluoro-phenoxy)-1H-pyrazolo[3,4-d]pyrimidin-4-ylarnino]-1-methyl-ethyl } ester; and 2-Amino-3-methyl-butyric acid 2-[3-(2-chloro-phenyl)-6-(2,4-difluoro-phenoxy)-1H-pyrazolo[3,4-d]pyrimidin-4-ylamino]-1-methyl-ethyl ester.

\* \* \* \* \*